United States Patent [19]

Brundidge et al.

[11] Patent Number: 4,714,760

[45] Date of Patent: * Dec. 22, 1987

[54] CEPHALOSPORIN INTERMEDIATES

[75] Inventors: Steven P. Brundidge, Wolcott; Paul R. Brodfuehrer, Syracuse; Chet Sapino, Jr.; Kun M. Shih, both of East Syracuse; Donald G. Walker, Liverpool, all of N.Y.

[73] Assignee: Bristol-Myers Company, New York, N.Y.

[ * ] Notice: The portion of the term of this patent subsequent to Apr. 21, 2004 has been disclaimed.

[21] Appl. No.: 882,107

[22] Filed: Jul. 11, 1986

Related U.S. Application Data

[63] Continuation-in-part of Ser. No. 767,561, Aug. 20, 1985, abandoned.

[51] Int. Cl.$^4$ .................................... C07D 501/18
[52] U.S. Cl. .................... 540/222; 540/224; 540/226
[58] Field of Search ................. 540/222, 224, 226

[56] References Cited

U.S. PATENT DOCUMENTS

| | | | |
|---|---|---|---|
| 4,104,391 | 8/1978 | Cise | 514/203 |
| 4,139,701 | 2/1979 | Berges | 540/222 |
| 4,168,309 | 9/1979 | Ayres | 540/222 |
| 4,182,863 | 1/1980 | Gottstein | 540/226 |
| 4,369,313 | 1/1983 | Jones | 540/224 |
| 4,406,899 | 9/1983 | Aburaki | 540/222 |
| 4,446,318 | 5/1984 | Naito | 540/226 |
| 4,499,088 | 2/1985 | Takaya | 540/222 |
| 4,540,779 | 9/1985 | Conrad | 540/224 |
| 4,659,812 | 4/1987 | Aburaki et al. | 540/222 |

FOREIGN PATENT DOCUMENTS 0054970 6/1982 European Pat. Off. ............ 540/224
2098216 11/1982 United Kingdom .

Primary Examiner—Sidney Marantz
Assistant Examiner—Robert Benson
Attorney, Agent, or Firm—Aldo A. Algieri

[57] ABSTRACT

Stable, crystalline cephalosporin intermediates of the formula

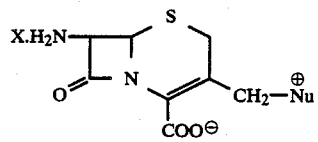

and

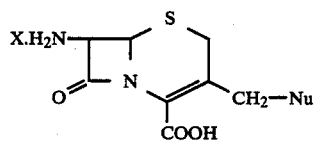

wherein X is HI or HCl and Nu and Nu$^\oplus$ are certain N-containing heterocyclic rings attached via a sulfur atom or a ring nitrogen atom, respectively, which are substantially free of the $\Delta^2$ isomer; processes for, and intermediates in, the preparation of the above compounds; and processes for the preparation of broad-spectrum cephalosporin antibiotics.

1 Claim, No Drawings

CEPHALOSPORIN INTERMEDIATES

CROSS-REFERENCE TO RELATED APPLICATION

This application is a continuation-in-part of our co-pending application Ser. No. 767,561, filed Aug. 20, 1985 abandoned.

SUMMARY OF THE INVENTION

This invention relates to temperature stable, crystalline salts of a cephalosporin intermediate having the formula

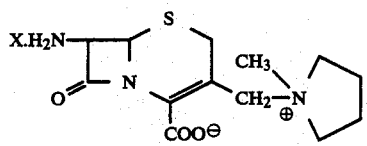

wherein X is HI or HCl, which are substantially free of the $\Delta^2$ isomer, and which are convertible into broad specturm cephalosporin antibiotics without the necessity of a carboxyl group deblocking step. This invention also relates to a method for making the salts of Formula I, to intermediates in the preparation of the salts of Formula I, and to a method of converting a salt of Formula I into broad spectrum cephalosporin antibiotics.

DESCRIPTION OF THE PRIOR ART

U.S. Pat. No. 4,406,899, issued Sept. 27, 1983 to Aburaki et al., discloses compounds of the formulae

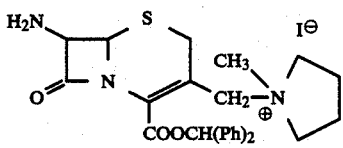

wherein Ph is phenyl, and

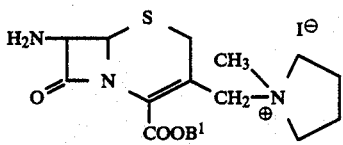

or an N-silyl derivative thereof, wherein $B^1$ is hydrogen or a conventional carboxyl-protecting group. These compounds are not exemplified in the patent, but are disclosed by structural formulae only, as intermediates in an alternate reaction scheme for the preparation of certain cephalosporins (by acylation and then deblocking of the protected carboxyl group). The reaction scheme actually exemplified did not utilize these compounds (and also required deblocking of the protected carboxyl group as the final step). Each of the final products of U.S. Pat. No. 4,406,899 required a chromatographic purification step to separate the mixture of $\Delta^2$ and $\Delta^3$ isomers which were produced.

U.S. Pat. No. 4,168,309, issued September 18, 1979 to Barry E. Ayres, discloses compounds of the formula

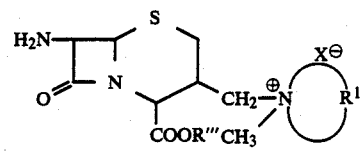

wherein $R'''$ is a carboxyl-protecting group; $R^1$, taken together with the carbon atom to which it is attached, forms an optionally substituted saturated or partially saturated 4-10 membered heterocyclic ring which may contain one or more further heteroatoms selected from O, N and S; the dotted line indicating a ceph-2-em or a ceph-3-em compound; and $X^-$ representing an anion; and acid addition salts or an N-silylated derivative thereof.

These compounds are not exemplified but are disclosed by structural formula only as intermediates in an alternative synthesis of certain cephalosporins (by acylation and then deblocking of the protected carboxyl group). The reaction scheme actually exemplified did not utilize these compounds (and also required deblocking of the protected carboxyl group as a final step).

The use of blocked carboxyl groups in the processes of the above two patents has the disadvantage of requiring deblocking after acylating whereby acyl group is lost in the deblocking step due to less than 100% yield in the deblocking step.

U.S. Pat. No. 4,223,135, issued September 16, 1980 to Derek WalKee et al., discloses compounds of the formula

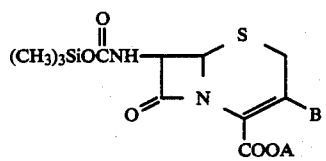

in which B is chloro, methoxy or $-CH_2E$, E is hydrogen,

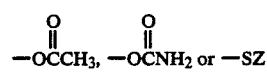

in which Z is an optionally substituted 5- or 6-membered heterocyclic ring containing 2-4 N atoms and zero or one atom selected from O and S, the S atom of -SZ being connected to a carbon atom of the heterocyclic ring Z, and A is trimethylsilyl or an easily cleavable ester-protecting group.

The compounds are prepared by adding dry carbon dioxide to a solution of a compound of the formula

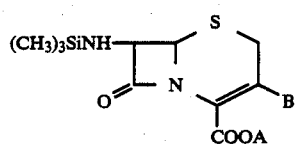

wherein A and B are as described above, in an inert organic solvent which is preferably methylene chloride.

U.S. Pat. Nos. 4,316,017, which is a continuation-in-part of a division of 4,223,135, has a substantially identical disclosure.

U.S. Pat. No. 4,336,253, issued June 22, 1982 to William H. W. Lunn, discloses compounds of the formula

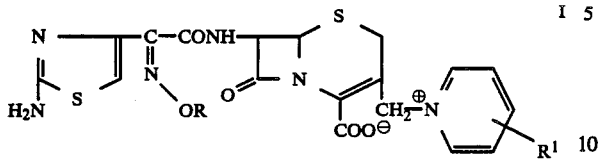

and their preparation by reaction of a compound of the formula

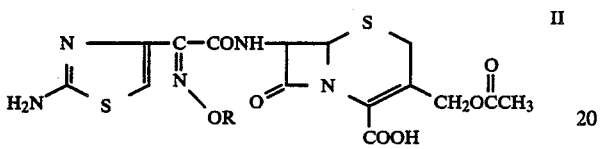

with a silylating agent such as trimethylsilylacetamide, bistrimethylsilylacetamide, or the like, to produce a compound of the formula

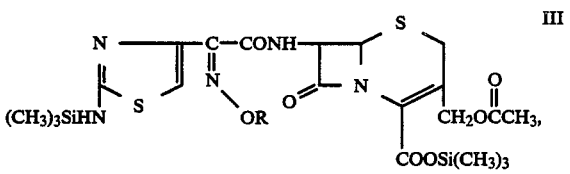

reacting the compound of Formula III with trimethylsilyl iodide to produce a compound of the formula

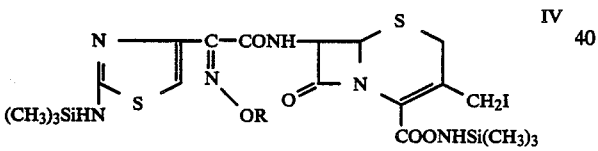

and then reacting the compound of Formula IV with

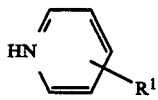

to produce a compound of Formula I.

Solvents suitable for the reactions to produce Compounds III and IV are stated to be chlorinated hydrocarbons and lower alkyl nitriles.

U.S Pat. Nos. 4,379,787, 4,382,931 and 4,382,932 to William H. W. Lunn et al. are to analogous compounds and processes, wherein R is, for example, an amino-substituted oxazole, oxadiazole or isoxazole ring, and the 3-substituent is, for example, optionally substituted pyridine, quinoline or isoquinoline.

South African Pat. No. 84/3343, issued Oct. 25, 1984, discloses a process for the preparation of cephalosporins of the formula

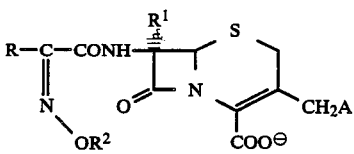

in which R is thiazolyl or 1,2,4-thiadiazolyl radical, $R^1$ is hydrogen or methoxy, $R^2$ is one of numerous substituents known in the cephalosporin art, and A is optionally substituted quinolinium, isoquinolinium or pyridinium. The compounds of Formula I are prepared by reacting a compound of the formula

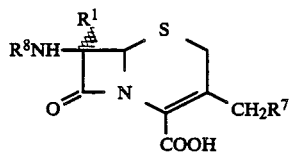

in which $R^8$ is hydrogen or an amino-protecting group and $R^7$ is "a group which can be replaced by the base corresponding to radical A", with the base corresponding to radical A in the presence of a trialkyliodosilane, to form a compound of the formula

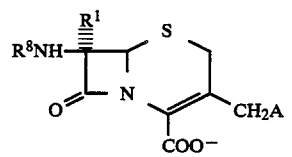

which (after removal of any amino-protective group) is subsequently acylated with an acid of the formula

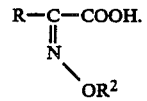

Suitable $R^7$ groups which are mentioned include acetoxy, propionyloxy, chloroacetoxy, acetylacetoxy and carbamoyloxy. Suitable solvents which are mentioned include methylene chloride, chloroform, dichloroethane, trichloroethane, carbon tetrachloride, acetonitrile, propionitrile and frigands. Methylene chloride is most preferred.

It is acknowledged in the patent that the general process is known, but it is stated that the inventors have found that the yields are surprisingly high if the nucleophilic displacement reaction on Compound II (to form Compound III) is carried out by first adding an excess of the base corresponding to radical A (up to a 20-fold excess) and then adding the trialkyliodosilane (up to a 10-fold excess).

In the W. German priority application No. (P3316798.2, filed May 7, 1983) for this S. African application, the solvents listed are the same as above, except that "frigand" is called "frigen". The Merck Index, 10th Edition, lists Frigen 11, Frigen 12 and Frigen 114, and shows them as other names for Freon 11, Freon 12 and Freon 114 which are trichlorofluoromethane, dichlorodifluoromethane and 1,2-dichloro-1,1,2,2-tetrafluoroethane, respectively.

COMPLETE DESCRIPTION

The compounds of the formula

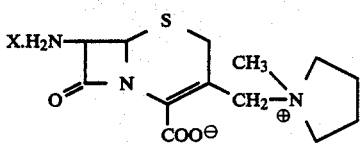

I wherein X is HI or HCl, when prepared as described herein, are crystalline, temperature stable and substantially free of the corresponding $\Delta^2$ isomer. As a result of being substantially free of the $\Delta^2$ isomer, they are convertible (by acylation) to broad spectrum cephalosporins which themselves are substantially free of the $\Delta^2$ isomer, without the need for chromatographic separation $\Delta^2$ and $\Delta^3$ isomers. As a result of their temperature stability, they may be isolated and stored, and converted to the end products when desired. An additional advantage of the intermediates of Formula I is that they do not require blocking (protection) of the carboxyl group prior to acylation or deblocking (deprotection) of the carboxyl group after acylation, thus offering process efficiency.

The compounds of Formula I may be prepared by treating a solution of the compound of the formula

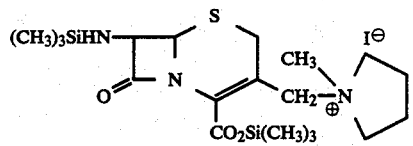

II in 1,1,2-trichlorotrifluoroethane (Freon TF) with a (lower)-alkanol or water to remove the trimethylsilyl groups, followed by HCl or HI to form the hydrochloride or hydriodide salt. It is preferred to use a (lower)alkanol for removal of the trimethylsilyl groups, and most preferably methanol. The reaction is conducted at a temperature of from about $-10°$ C. to about 25° C., and preferably at a temperature of from about 0° C. to about 10° C. From about 2 to about 5 equivalents of methanol are used per equivalent of Compound II, and preferably about 3 to about 4 equivalents of methanol.

The compound of Formula II may be prepared by reacting a solution of the compound of the formula

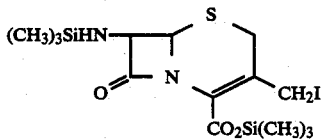

IIIa in Freon TF with N-methylpyrrolidine (NMP). It has surprisingly been found that the use of Freon TF as solvent produces Compound II which is substantially free of the $\Delta^2$ isomer, while commonly used solvents such as methylene chloride, carbon tetrachloride, chloroform or dioxane produce Compound II which contains large amounts of the undesirable $\Delta^2$ isomer (e.g. 50% $\Delta^2$ isomer).

The reaction is conducted at a temperature of from about $-10°$ C. to about 25° C., and preferably from about 0° C. to about 10° C. Although it is possible to use greater or lesser amounts of N-methylpyrrolidine, we obtain highest purity of product when about 1 equivalent of NMP is utilized per equivalent of Compound IIIa.

The compound of Formula IIIa may be prepared by reaction of a solution of the compound of the formula

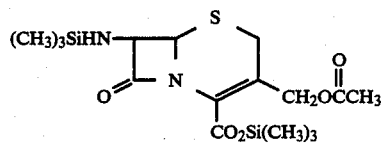

IVa in Freon TF or methylene chloride, with trimethylsilyl iodide (TMSI). Surprisingly, these solvents yield Compound IIIa which
is substantially free of the $\Delta^2$ isomer, while similar common solvents (e.g. 1,2-dichloroethane) give Compound IIIa containing significant amounts of the undesirable $\Delta^2$ isomer (e.g. 25%). Other common solvents such as chlorobenzene, dioxane, carbon tetrachloride, and the like, also give significant amounts of the undesirable $\Delta^2$ isomer.

The reaction is conducted at a temperature of from about 5° C. to about 40° C., but preferably is conducted at ambient temperature for convenience. The TMSI may be utilized in an amount of from about 0.9 to about 1.5 equivalents per equivalent of Compound IVa. We prefer to use from about 1.0 to about 1.2 equivalents of TMSI.

The compound of Formula IVa may be prepared by reacting 7-aminocephalosporanic acid (7-ACA), i.e. the compound of the formula

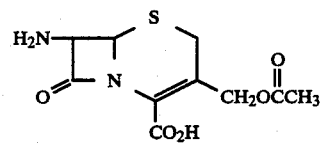

V with hexamethyldisilazane (HMDS) in the presence of from about 0.01 to about 0.1 equivalents of TMSI per equivalent of 7-ACA, in Freon TF or methylene chloride, at a temperature from room temperature to the boiling point of the solvent. Preferably, the reaction is conducted at reflux. The HMDS may be used in an amount of from about 0.95 to about 1.4 equivalents per equivalent of 7-ACA, and preferably from about 1.0 to about 1.3 equivalents of HMDS per equivalent of 7-ACA. We most prefer to utilize 1.2 equivalents of HMDS.

In an alternate preparation of Compound II, a solution of Compound IVa in Freon TF is reacted with N-methyl-N-trimethyl-silylpyrrolidinio iodide having the formula

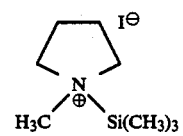

VI at a temperature of from about 10° C. to about 40° C. For convenience, we prefer to conduct the reaction at 35° C. The compound of Formula VI may be used in an amount of from about 1.0 to about 2.0 equivalents per equivalent of Compound IVa, and preferably from about 1.2 to about 1.5 equivalents of Compound VI per equivalent of Compound IVa. If desired, a small amount of imidazole (e.g. 0.1 equivalents) may be added to the reaction mixture to shorten the reaction time. We have found that, when preparing Compound II by the reaction of Compound IVa with Compound VI, Compound IIIA can be detected in the reaction mixture during the reaction in small amounts (by NMR analysis).

The compound of Formula VI may be prepared by reacting N-methylpyrrolidine with about an equimolar amount of TMSI in Freon TF as solvent, at a temperature of from about −10° C. to about 25° C. We prefer to conduct the reaction at a temperature of from about 0° C. to about 5° C. The reaction ratio of NMP and TMSI may be varied, but we obtain excellent results by utilizing equimolar amounts.

In a preferred reaction scheme, the compounds of Formula I are prepared from 7-ACA in a "one pot" reaction, i.e. without the isolation of any intermediates. Although certain of the individual reaction steps may be conducted in solvents other than Freon TF, as indicated above, others require the use of Freon TF. Accordingly, when conducting the "one pot" reaction, the reaction is conducted in Freon TF.

In conducting the reaction sequence described herein, we have found it necessary to proceed via the 3-iodomethyl Compound IIIa, rather than the corresponding 3-chloromethyl or 3-bromomethyl analog. We have surprisingly found that the reaction of Compound IVa with trimethylsilyl chloride or trimethylsilyl bromide gives little of the expected 3-chloromethyl or 3-bromomethyl analog of Compound IIIa, e.g. a maximum of about 5-15% even after refluxing for 10 days.

Although the quaternization of Compound IIIa with NMP to produce Compound II (and, subsequently, a compound of Formula I), must be conducted in Freon TF in order to obtain Compound II (and I) which are substantially free of the $\Delta^2$ isomer, Compound IIIa may be reacted with other nucleophilic agents in Freon TF or methylene chloride solution to produce analogs of Compound II. After treatment with a (lower)alkanol and optional salt formation with, for example, HCl or HI, there are obtained analogs of Compound I which have the formula

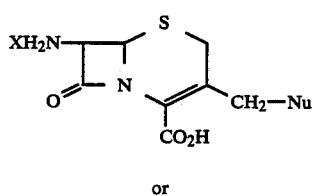

or

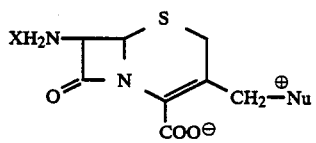

in which X is, for example, HCl or HI, —Nu is

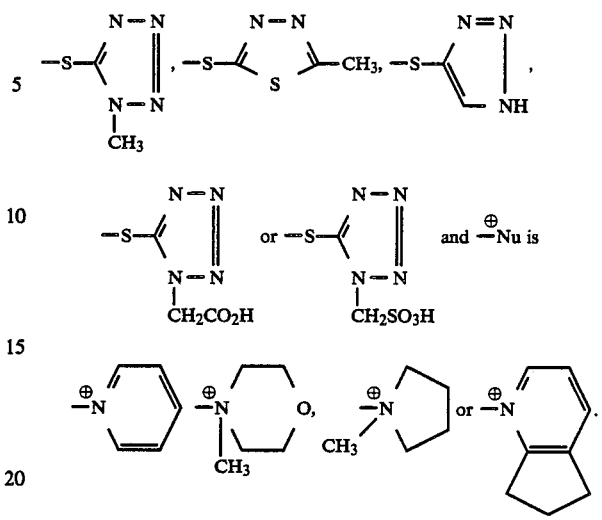

and $-\overset{\oplus}{Nu}$ is

The compounds of Formula VIIa and VIIb also may be prepared by the reaction of the compound of the formula

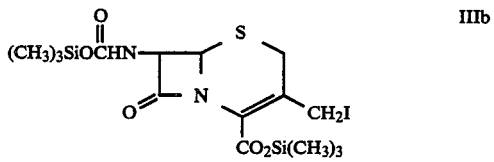

by the same procedure described above for their preparation from Compound IIIa. However, the compound of formula IIIb is highly insoluble in Freon TF, so that the reaction must be conducted in methylene chloride. For that reason, when prepared from Compound IIIb, the compounds of Formula VIIb in which $-\overset{\oplus}{Nu}$ is the N-methylpyrrolidinio moiety (i.e. the compounds of Formula I) are predominantly the undesirable $\Delta^2$ isomer.

The compound of Formula IIIb may be prepared, in Freon TF or methylene chloride, from the compound of the formula

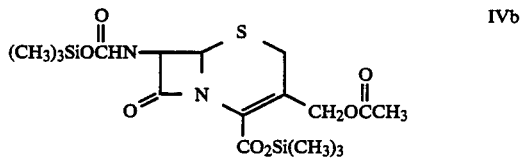

by the same procedure described above for the preparation of Compound IIIa from Compound IVa. The compound of Formula IVb may be prepared by bubbling carbon dioxide gas into a solution of Compound IIIa in Freon TF or methylene chloride, in the presence of a small amount (e.g. 0.1 equivalent) of pyridine hydrochloride.

The compounds of Formula I, VIIa and VIIb are readily converted to broad spectrum antibiotics by acylation with the appropriate side-chain acid. For example, a compound of Formula I (X =HCl or HI) is converted to 7-[α-(2-aminothiazol-4-yl) -α-(Z)-methoxyiminoacetamido]-3-[(1-methyl-1-prrolidinio)-methyl] -3-cephem-4-carboxylate (VIII) by N-acylating with 1-benzotriazolyl (Z)-2-(2-aminothiazol-4-yl)-2-methoxyiminoacetate active ester. The reaction equation is set forth below.

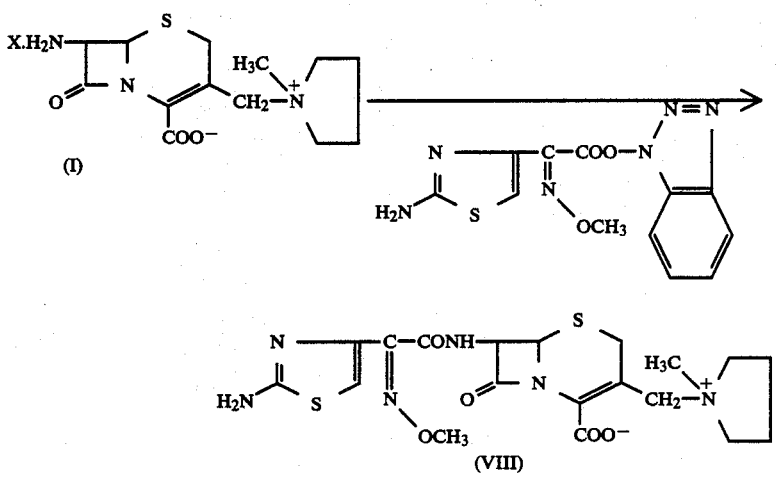

This reaction is readily carried out in the presence of N,N-dimethylaniline in dimethylformamide at room temperature over a period of 10–20 hours; or by dissolving (I) in water and dimethylformamide and adding sodium bicarbonate with ice cooling, and reacting at room temperature for about 30 minutes to about 5 hours; or by dissolving (I) in water, cooling to 5°–15° C., adding NaOH dropwise to pH 5.5–6, adding tetrahydrofuran, adding sodium hydroxide to adjust the pH to 6.7–6.9, adding the active ester reactant and reacting for 1 to 5 hours at room temperature. The active ester is a known compound and is described in Hoechst, Japan Kokai No. 54-95593 (7/28/79) and German Application No. 2758000.3 (12/24/77). The utility of the compound (VIII) is shown in Aburaki et al., U.S. Pat. No. 4,406,899.

The compounds of Formulae VIIa and VIIb may be acylated in a similar manner to produce broad spectrum cephalosporins.

EXAMPLE 1

(6R,7R)-Trimethylsilyl 7-(Trimethylsilyl)amino-3-acetoxymethylceph-3-em-4-carboxylate

Method A

An oven-dried flask and Friedrich's condenser were cooled to ambient temperature under a stream of dry nitrogen. The flask was then charged with 50.0 g (184 mmoles) of 7-ACA (97.2% purity) and 400 ml of dry 1,1,2-trichlorotrifluoroethane (Freon TF, dried over molecular sieves). To the resulting slurry was added 46.5 ml (222 mmoles, 1.2 equivalents) of 98% 1,1,1,3,3,3-hexamethyldisilazane (HMDS) and 0.80 ml (5.6 mmoles, 0.03 equivalents) of iodotrimethylsilane (TMSI) with good stirring and with protection from moisture. The slurry was vigorously heated under reflux for 16–18 hours, after which time it was cooled to ambient temperature. A $^1$H NMR spectrum of an aliquot of the slightly hazy reaction mixture showed >95% conversion to the desired product. NMR (CD$_2$Cl$_2$, 360 MHz) δ0.23 (s, 9H, N-Si(CH$_3$)$_3$), 0.38 (s, 9H, —COO-Si(CH$_3$)$_3$), 0.38 (s 9H, COOSi(CH$_3$)$_3$), 1.51 (d, 1H, J=13.6 Hz, NH—), 2.09 (s, 3H, —COCH$_3$), 3.41 (d, 1 H, J=18.3 Hz, —SCH$_2$—), 3.61 (d, 1H, J=18.3 Hz, —SCH$_2$), 4.80 (dd, 1 H, J=4.5, 13.6 Hz, —COCH(N-HSi(CH$_3$)$_3$), 4.83 (d, 1H, J=13.2 Hz, —CH$_2$OCOCH$_3$), 4.91 (d, 1H, J=4.5 Hz, —COCH(NHSi(CH$_3$)$_3$CH—), 5.11 (d, 1H, J=13.2 Hz, —CH$_2$OCOCH$_3$).

Method B

An oven-dried flask and Friedrich's condenser were cooled to ambient temperature under a stream of dry nitrogen. The flask was charged with 10.0 g (36.7 mmoles) of 7-ACA (97.2% purity) and 80 ml of dry Freon TF (dried over molecular sieves). To the resulting slurry was added 9.3 ml (44.1 mmoles, 1.2 equivalents) of 98% HMDS and 44 ml (1.1 mmoles, 0.03 equivalent) of a 0.025M solution of HI in Freon TF (prepared by bubbling HI into dry Freon TF and titrating the resulting saturated solution to a phenolphthalein endpoint). The slurry was vigorously heated under reflux with good stirring and with protection from moisture for 22 hours, after which time it was cooled to ambient temperature. A $^1$H NMR spectrum (CD$_2$Cl$_2$, 360 MHz showed >95% conversion to the desired product.

Method C

An oven-dried flask and Friedrich's condenser were cooled to ambient temperature under a stream of dry nitrogen. The flask was charged with 10.0 g (36.7 mmoles) of 7-ACA (97.2% purity) and 80 ml of dry dichloromethane (from sieves). To the resulting slurry was added 9.3 ml (44.1 mmoles, 1.2 equivalents) of 98% HMDS and 0.16 ml (1.1 mmoles, 0.03 equivalent) of TMSI with good stirring and with protection from moisture. The slurry was vigorously heated under reflux for 5 hours, after which time the slightly hazy reaction mixture was cooled to ambient temperature A $^1$H NMR spectrum (CD$_2$Cl$_2$, 360 MHz) showed >95% conversion to the desired product.

EXAMPLE 2

(6R,7R)-Trimethylsilyl 7-[((Trimethylsilyl)oxy)carbonyl]amino-3-acetoxymethylceph-3-em-4-carboxylate

Method A

To a reaction mixture of (6R,7R)-trimethylsilyl 7-(trimethylsilyl)amino-3-acetoxymethylceph-3-em-4-carboxylate in Freon TF (prepared according to Method A of Example 1; 10.0 g input 7-ACA) was added 410 mg (3.5 mmoles, 0.10 equivalent) of freshly prepared pyridine hydrochloride under a blanket of dry nitrogen at ambient temperature. Next, dry carbon dioxide gas was gently bubbled into the reaction mixture through a capillary pipet for 24 hours with good stirring. After this time, the resulting slurry was filtered with positive nitrogen pressure through a Schlenk funnel, and the collected solid was washed with fresh, dry Freon TF (2×25 ml) and was partially dried under suction with a positive stream of nitrogen for 15 minutes. Further drying at ambient temperature at 0.05 mm Hg for 5 hours gave 13.30 g (85%) of light yellow, crystalline, moisture sensitive (6R,7R)-trimethylsilyl 7-[((trimethylsilyl)oxy)carbonyl]amino-3-acetoxymethylceph-3-em-4-carboxylate: $IR(CH_2Cl_2)$ 1790, 1743, 1709, 1511, 1250, 1232 $cm^{-1}$; $NMR(CD_2Cl_2, 360 MHz)$ $\delta 0.31$ (s, 9H, —$NHCOOSi(CH_3)_3$), 0.36 (s, 9H, —$COOSi(CH_3)_3$), 2.08 (s, 3H, —$COCH_3$), 3.44 (d, 1H, J=18.6 Hz, —$SCH_2$), 3.63 (d, 1H, J=18.6 Hz, —$SCH_2$), 4.85 (d, 1H, J=13.4 Hz, —$CH_2OAc$), 5.02 (d, 1H, J=5.1 Hz, —CHCH(—N)$SCH_2$), 5.11 (d, 1 H, J=13.4 Hz, —$CH_2OAc$), 5.54 (d, 1H, J=9.7 Hz, —CONHCH(CO—)CH—), 5.63 (dd, 1H, J=5.1, 9.7 Hz, —CONHCH(CO—)CH—).

Method B

Dry carbon dioxide gas was gently bubbled into a reaction mixture of (6R,7R)-trimethylsilyl 7-(trimethylsilyl)amino-3-acetoxymethylceph-3-em-4-carboxylate in dry dichloro-methane (prepared according to Method C of Example 1; 5.0 g input 7-ACA) with good stirring for 12 hours at ambient temperature. A $^1H$ NMR spectrum of an aliquot of the resulting solution showed >95% conversion to the desired (6R,7R)-trimethylsilyl 7-[((trimethylsilyl)oxy)carbonyl]amino-3-acetoxymethylceph-3-em-4-carboxylate.

EXAMPLE 3

(6R,7R)-Trimethylsilyl 7-(Trimethylsilyl)amino-3-iodomethylceph-3-em-4-carboxylate

Method A

A total of 30 ml (210 mmoles, 1.15 equivalents) of TMSI was added in a slow stream at ambient temperature to a reaction mixture of (6R,7R)-trimethylsilyl 7-(trimethylsilyl)amino-3-acetoxymethylceph-3-em-4-carboxylate in Freon TF (prepared according to Method A of Example 1; 50.0 g input 7-ACA) under a blanket of dry nitrogen. The progress of the reaction was monitored by $^1H$ NMR (acetate region). After 1 hour, the slurry was filtered through a Schlenk tube under positive nitrogen pressure. The collected solid was washed with fresh Freon TF (1 ×100 ml). An aliquot of the filtrate gave the following $^1H$ NMR spectrum in support of the in situ generated (6R,7R)-trimethylsilyl 7-(trimethylsilyl)amino-3-iodomethylceph-3-em-4-carboxylate: ($CD_2Cl_2$, 360 MHz) $\delta$ .16 (s, 9H, $NHSi(CH_3)_3$), 0.40 (s, 9H, —$COOSi(CH_3)_3$), 1.51 (d, 1H, J=13.4 Hz, NH), 3.54 (d, 1H, J=17.9 Hz, —$SCH_2$—), 3.80 (d, 1H, J=17.9 Hz, —$SCH_2$), 4.37 (d, 1H, J=9.2 Hz, —$CH_2I$), 4.49 (d, 1H, J=9.2 Hz, —$CH_2I$), 4.75 (dd, 1H, J=4.6, 13.4 Hz, —COCH($NHSi(CH_3)_3$), 4.89 (d, 1H, J=4.6 Hz, —COCH($NHSi(CH_3)_3$)CH—).

Method B

To a stirred solution of (6R,7R)-trimethylsilyl 7-(trimethylsilyl)amino-3-acetoxymethylceph-3-em-4-carboxylate in dichloromethane (prepared according to Method C of Example 1; a 20 ml aliquot of the reaction mixture (11.7 mmoles starting material content was used for this reaction) under a blanket of nitrogen at ambient temperature was added 1.66 ml (11.7 mmoles, 1.0 equivalent) of iodotrimethylsilane (TMSI) in a slow stream. After stirring for an additional 1 hour, the $^1H$ NMR spectrum (acetate region) of an aliquot showed >95% conversion to the desired (6R,7R)-trimethylsilyl 7-(trimethylsilyl)amino-3-iodomethlceph-3-em-4-carboxylate.

EXAMPLE 4

(6R,7R)-Trimethylsilyl 7-[((Trimethylsilyl)oxy)carbonyl]amino-3-iodomethyl-ceph-3-em-4-carboxylate To a stirred solution of (6R,7R)-trimethylsilyl 7-[(trimethylsilyl) oxy)carbonyl]amino-3-acetoxymethylceph-3-em-4-carboxylate in dichloromethane (prepared according to Method B of Example 2; 5.0 g input 7-ACA was added 3.0 ml (21.1 mmoles, 1.15 equivalents) of TMSI in a slow stream at ambient temperature under a blanket of dry nitrogen. The progress of the reaction was monitored by $^1H$ NMR (acetate region). After a total of 65 minutes, the $^1H$ NMR spectrum of an aliquot of the dark solution showed >95% conversion to the desired (6R,7R)-trimethylsilyl 7-[((trimethylsilyl)oxy)-carbonyl]amino-3-iodomethylceph-3-em-4-carboxylate: NMR ($CD_2Cl_2$) $\delta 0.27$ (br s, 9H —$NHCOOSi(CH_3)_3$), overlapped with $CH_3COOSi(CH_3)_3$), 0.37 (s, 9H, —$COOSi(CH_3)_3$), 3.57 (d, 1H, J=18.1 Hz, —$SCH_2$), 3.80 (d, 1H, J=18.1 Hz, —$SCH_2$), 4.34 (d, 1H, J=9.2 Hz, —$CH_2I$), 4.51 (d, 1 H, J=9.2 Hz, —$CH_2I$), 5.00 (d, 1H, J=4.6 Hz, —COCH(N)CH(N)$SCH_2$—); the remainder of the spectrum was obliterated by protonic dichloromethane.

EXAMPLE 5

N-Methyl-N-trimethylsilylpyrrolidinio Iodide

An oven-dried flask was cooled to ambient temperature under a stream of positive nitrogen. The flask was charged with 25 ml of dry Freon TF (dried over molecular sieves) and 1.42 ml (10.0 mmoles, 1.0 equivalent) of TMSI. The resulting solution was cooled to 0-5° C. under a blanket of dry nitrogen. A total of 1.04 ml (10.0 mmoles, 1.0 equivalent) of dry, 97% N-methylpyrrolidine (dried over molecular sieves) was added dropwise and the resulting slurry was stirred at 0°-5° C. under a nitrogen blanket for 30 minutes. After this time, the slurry was filtered under positive nitrogen pressure through a Schlenk funnel, and the collected solid was washed with fresh, dry Freon TF (2×25 ml). The filter cake was partially dried under a positive stream of nitrogen for 15 minutes. Further drying at ambient temperature for 12 hours at 0.05 mm Hg afforded 2.51 g (89%) of N-methyl-N-trimethylsilylpyrrolidinio iodide as a colorless, extremely air sensitive solid: $C_8H_{20}INSi$ requires 44.49% iodide; found, 44.40% iodide (iodide ion chromatography analysis).

In a separate experiment, the reaction was conducted generally as above, except that 0.40 ml (10.0 mmoles, 1.0 equivalent) of methanol was added dropwise to the slurry of the salt in Freon TF at 0°-5° C. The resulting heterogeneous mixture was stirred at 0°-5° C. under a nitrogen blanket for an additional 30 minutes. The slurry was filtered under anhydrous conditions through a Schlenk funnel. The filter cake was washed with fresh Freon TF (2×25 ml) and was dried at ambient temperature for 3 hours at 0.05 mm Hg. The isolated solid (1.93 g, 91%) was identified as N-methylpyrrolidinio iodide, mp 80°-82° C. (uncorrected). An authentic sample of this salt was prepared independently by gassing a solution of N-methylpyrrolidine in Freon TF with hydrogen iodide. The isolated solid had mp 83.5°-85.5° C. (uncorrected). The 360 MHz $^1$H NMR spectrum of this material (D$_2$O) was consistent with the spectrum observed for the salt isolated from the methanol quenched reaction.

The 360 MHz $^1$H NMR spectrum of the filtrate from the methanol quenched reaction showed, as the major components, methoxytrimethylsilane and methyl iodide (integration ratio 17/1), as well as a small amount of hexamethyldisiloxane.

EXAMPLE 6

(6R,7R)-7-Amino-3-(1-methyl-1-pyrrolidinio)methylceph-3-em-4-carboxylate Monohydrochloride

Method A

To a solution of (6R,7R)-trimethylsilyl 7-(trimethylsilyl)amino-3-iodomethylceph-3-em-4-carboxylate in Freon TF (prepared according to Method A of Example 3; 50.0 g input 7-ACA) at 0°-5° C. under a blanket of dry nitrogen was added 19.0 ml (183 mmoles, 1.0 equivalent) of dry 97% N-methylpyrrolidine (NMP, dried over molecular sieves) dropwise at a rate sufficient to maintain a reaction temperature of <10° C. The resulting slurry was stirred vigorously at 0°-5° C. for 15 minutes following complete addition. After this time, an additional 100 ml of dry Freon TF was added to facilitate agitation. Next, 25 ml (615 mmoles, 3.35 equivalents) of methanol was added dropwise at a rate sufficient to maintain a reaction temperature of <10° C. The slurry was vigorously stirred at 0°-5° C. for an additional 15 minutes. The reaction mixture was filtered and the collected solid was washed with fresh Freon TF (1×100 ml) followed by partial drying under suction for 15 minutes. Further drying in vacuo at ambient temperature for 16 hours gave 71.3 g (>100%) of crude product.

To this material was added 200 ml of water. The pH of the slurry (2.40) was lowered to 0.50 by dropwise addition of concentrated HCl. A total of 10.0 g of decolorizing carbon was added, and the slurry was stirred at ambient temperature for 15 minutes. The decolorizing carbon was removed by filtration through a celite pad (10.0 g), and the pad was washed with fresh deionized water (1×25 ml). The product was precipitated from the aqueous solution by dropwise addition of 5 volumes of acetone. The slurry was cooled to 0°-5° C. and was maintained at this temperature for 30 minutes. The slurry was vacuum filtered, sequentially washed with 50 ml of cold (0°-5° C.) 5/1 acetone/water and acetone (2×50 ml), and was partially dried under suction for 15 minutes. Further drying in vacuo afforded 23.3 g (39%) of snow white, crystalline (6R,7R)-7-amino-3-(1-methyl-1-pyrrolidinio)-methylceph-3-em-4-carboxylate monohydrochloride: HPLC assayed as 96.3% versus the standard lot; NMR (D$_2$O, , 360 MHz, D$_2$O/H$_2$O supressed) δ2.14-2.32 (envelope, 4H, —N(CH$_3$)CH$_2$CH$_2$—), 3.00 (s, 3H, NCH$_3$), 3.46-3.67 (m, 5H, —N(CH$_3$)CH$_2$CH$_2$; SCH$_2$), 3.96 (d, 1H, J=16.9 Hz, —SCH$_2$), 4.09 (d, 1H, J=13.9 Hz, =CCH$_2$N—), 4.73 (d, 1H, J=13.9 Hz, =CCH$_2$N—), 5.21 (d, 1H, J=5.1 Hz, —COCHCHS—), 5.41 (d, 1H, J=5.1 Hz, —COCHCHS—).

Method B

An oven-dried flask was cooled to ambient temperature under a stream of dry nitrogen. The flask was charged with 15.7 ml (110 mmoles, 1.5 equivalents) of TMSI and 140 ml of dry Freon TF (dried over molecular sieves). The resulting solution was cooled to 0°-5° C., and 10.7 ml (103 mmoles, 1.4 equivalents) of 97% NMP was added dropwise so as to maintain a reaction temperature of <10° C. Following the addition, the slurry was stirred at 0°-5° C. for 30 minutes under a nitrogen blanket. After this time, the slurry was allowed to warm to room temperature.

A reaction mixture containing (6R,7R)-trimethylsilyl 7-(trimethylsilyl)amino-3-acetoxymethylceph-3-em-4-carboxylate (prepared according to Method A of Example 1; 20.0 g input 7-ACA) was added by cannula as quickly as possible to the NMP/TMSI slurry at ambient temperature. The resulting heterogeneous mixture was stirred at room temperature for 14 days with periodic monitoring of the reaction progress by HPLC. At a point where the 7-ACA area % was <2% of the total peak area, methanol (6.0 ml, 147 mmoles, 2.0 equivalents) was added dropwise and stirring was continued for an additional 30 minutes. The crude product was filtered, washed with fresh Freon TF (1×300 ml), and was partially dried under suction for 15 minutes. The product was further dried in vacuo at ambient temperature for 16 hours.

The crude product was slurried in 80 ml of deionized water. The pH was lowered to 0.50 by dropwise addition of concentrated HCl with good stirring. Decolorizing carbon (20% by weight of the crude product) was added, and the mixture was stirred for an additional 45 minutes. The slurry was vacuum filtered through diatomaceous earth, and the pad was washed with deionized water. Isopropyl alcohol (IPA, 900 ml) was added dropwise over a period of 1 hour to the aqueous phase with moderate agitation. The resulting slurry was stirred at 25° C. for 1 hour, cooled to 0°-5° C. and was stirred for an additional 1 hour. Filtration, washing with cold (0°-5° C.) 9/1 IPA/water (1×200 ml) and acetone (1×200 ml) and drying at 25° C. in vacuo for 16 hours gave 15.5 g (63%) of crystalline (6R,7R)-7-amino-3-(1-methyl-1-pyrrolidinio)methylceph-3-em-4-carboxylate monohydrochloride.

Method C

As an adjunct to the procedure of Method B, imidazole (0.50 g, 7.3 mmoles, 0.10 equivalent) was added to the N-methylpyrrolidine/iodotrimethylsilane/Freon TF slurry at 0°-5° C. This modification resulted in a modest increase in reaction rate as the 7-ACA level reached <2% of the total HPLC peak area after 10 days. Processing of the reaction mixture as described in Method B above afforded 14.7 g (60%) of crystalline (6R,7R)-7-amino-3-(1-methyl-1-pyrrolidinio)methylc 3-em-4-carboxylate monohydrochloride.

Method D

To a slurry of (6R,7R)-trimethylsilyl 7-(trimethylsilyl)amino-3-(1-methyl-1-pyrrolidinio)methylceph-3-em-4-carboxylate iodide in Freon TF (prepared according to Method A of Example 6; 20.0 g input 7-ACA) at 0°-5° C. under a blanket of dry nitrogen was added 10 ml (246 mmoles, 3.35 equivalents) of methanol dropwise over 5 minutes (Temperature <9° C.). The resulting slurry was stirred at 0°-5° C. for 15 minutes following the addition. Next, 50 ml of 3 N HCl (prepared by adding 250 ml of concentrated HCl to 756 ml of deionized water) was added dropwise over a period of 10 minutes. Following the addition, the cooling bath was removed and the mixture was stirred for 15 minutes. The phases were separated, and the aqueous phase (brought to a volume of 100 ml) was stirred for 30 minutes at ambient temperature with 4.0 g (20% of weight of input 7-ACA) of decolorizing carbon. The slurry was filtered through 4.0 g of diatomaceous earth, and the pad was washed with deionized water (1×10 ml). The aqueous volume was brought to 100 ml.

Crystallization Method 1: To 50 ml of the rich aqueous was added 250 ml (5 volumes) of acetone dropwise to precipitate the product. The resulting slurry was stirred with ice water cooling for 1 hour, after which time it was filtered under suction, washed with cold (0°–5° C.) 5/1 acetone/water (2×40 ml) and acetone (1×40 ml) and was partially dried under suction for 15 minutes. The product was further dried in vacuo at ambient temperature for 15 hours to give 4.48 g (37%, based on 50% of the theoretical yield for 20.0 g input 7-ACA) of colorless, crystalline (6R,7R)-7-amino-3-(1-methyl-1-pyrrolidinio)methylceph-3-em-4-carboxylate monohydrochloride.

Crystallization Method 2: To 50 ml of the rich aqueous was added 150 ml (3 volumes) of isopropyl alcohol (IPA) dropwise to precipitate the product. The resulting slurry was stirred with ice water cooling for 1 hour, after which time it was filtered under suction, washed with cold (0°–5° C.) 9/1 IPA/water (2×40 ml) and acetone (1×40 ml), and was partially dried under suction for 15 minutes. The product was further dried in vacuo at ambient temperature for 15 hours to give 5.46 g (45%, based on 50% of the theoretical yield for 20.0 g input 7-ACA) of slightly off-white, crystalline (6R,7R)-7-amino-3-(1-methyl-1-pyrrolidinio)methylceph-3-em-4-carboxylate monohydrochloride.

Method E

To a solution of (6R,7R)-trimethylsilyl 7-(trimethylsilyl)amino-3-iodomethylceph-3-em-4-carboxylate in dichloromethane (prepared according to Method B of Example 3) at 0°–5° C. under a blanket of dry nitrogen was added 1.21 ml (11.7 mmoles, 1.0 equivalent) of dry, 97% N-methylpyrrolidine (dried over molecular sieves) dropwise such that the temperature was <10° C. Following the addition, the slurry was stirred at 0°–5° C. for 15 minutes. Next, 0.95 ml (23.5 mmoles, 2.0 equivalents) of methanol was added dropwise (<10° C.), and stirring was continued at 0°–5° C. for 15 minutes. The solid was isolated by suction filtration, washed with methanol (1×50 ml), dichloromethane (1×50 ml) and was dried in vacuo at ambient temperature to yield 2.65 g (76%) of crude (6R,7R)-7-amino-3-(1-methyl-1-pyrrolidinio)methylceph-3-em-4-carboxylate (as the iodide salt) as a light tan solid. The 360 MHz $^1$H NMR spectrum of this material showed a mixture of $\Delta^2$ and $\Delta^3$ isomers in a ratio of 65/35, respectively.

Method F

To a solution of (6R,7R)-trimethylsilyl 7-[((trimethylsilyl)oxy)carbonyl]amino-3-iodomethylceph-3-em-4-carboxylate in dichloromethane (prepared according to Example 4; 10.0 g input 7-ACA) at 0°–5° C. under a blanket of dry nitrogen was added 3.7 ml (35.7 mmoles, 1.0 equivalent) of dry, 97% N-methylpyrrolidine (dried over molecular sieves) dropwise such that the temperature remained <10° C. Following the addition, the dark solution was stirred for an additional 15 minutes at 0°–5° C. After this time, 2.9 ml (71.4 mmoles, 2.0 equivalents) of methanol was added dropwise (evolution of $CO_2$ noted), and the resulting slurry was stirred for 5 minutes. A total of 50 ml of fresh dichloromethane was added, and the reaction mixture was filtered under suction. The filter cake was washed with dichloromethane (3×50 ml) and was partially dried under suction for 20 minutes. Further drying in vacuo at ambient temperature for 17 hours gave 12.61 g (83%, as the hydriodide salt) of a 6/1 $\Delta^2/\Delta^3$ mixture (HPLC area % ratio) of (6R,7R)-trimethylsilyl 7-amino-3-(1-methyl-1-pyrrolidinio)methylceph-3-em-4-carboxyate.

EXAMPLE 7

(6R,7R)-7-Amino-3-[(1H-1-methyltetrazol-5-yl)thio]methylceph-3-em-4-carboxylic Acid

Method A

To a stirred solution of (6R,7R)-trimethylsilyl 7-(trimethylsilyl)amino-3-iodomethylceph-3-em-4-carboxylate in Freon TF (prepared according to Method A of Example 3; 2.50 input 7-ACA) at 0°–5° C. under a blanket of dry nitrogen was added a solution of 1.07 g (9.2 mmoles, 1.0 equivalent) of 1H-1-methyl-5-mercaptotetrazole and 0.74 ml (9.2 mmoles, 1.0 equivalent) of dry pyridine (dried over KOH) in 20 ml of dry dichloromethane (from sieves) dropwise over 10 minutes. The resulting mixture was stirred at 0°–5° C. for an additional 30 minutes following the addition. After this time, 1.5 ml (37 mmoles, 4.0 equivalents) of methanol was added dropwise over 10 minutes, and stirring was continued for an additional 10 minutes at 0°–5° C. The solid was collected by suction filtration, washed with fresh Freon TF (2×10 ml) and dried to constant weight in vacuo to yield 3.4 g (>100%) of crude product.

This material was slurried in 10 ml of water, cooled to 0°–5° C. and the pH was lowered to 0.50 by dropwise addition of 4 N HCl solution. To the resulting cloudy solution was added 0.50 g of decolorizing carbon, and stirring was continued for 15 minutes. The slurry was filtered through diatomaceous earth, and the pad was washed with water (1×5 ml). The filtrate was cooled to 0°–5° C. and the pH was raised to 4.0 by dropwise addition of 6 N NaOH solution. The resulting slurry was stirred for 1 hour at 0°–5° C. The solid was collected by suction filtration, washed with cold (0°–5° C.) water (2×5 ml) and was dried to constant weight in vacuo to give 1.3 g (43%) of 7-amino-3 -[(1H-1-methyltetrazole-5-yl)thio]methylceph-3-em-4-carboxylic acid. The 360 MHz $^1$H NMR spectrum and HPLC chromatogram of this material were consistent with those of an authentic sample prepared independently.

Method B

To a stirred solution of (6R,7R)-trimethylsilyl 7-[((trimethylsilyl)oxy)carbonyl]amino-3-iodomethylceph-3-em-4-carboxylate in dichloromethane (prepared according to Example 4; 5.0 g input 7-ACA) at 0°–5° C. under a blanket of dry nitrogen was added a suspension consisting of 2.13 g (18.4 mmoles, 1.0 equivalent) of 1H-1-methyl-5-mercaptotetrazole and 1.49 ml (18.4 mmoles, 1.0 equivalent) of dry pyridine (dried over KOH) in 20 ml of dichloromethane dropwise over 5 minutes. The mixture was stirred for an additional 90 minutes at 0°–5° C. following the addition. After this time, 2.50 ml (61.5 mmoles, 3.35 equivalents) of methanol was added dropwise over 2 minutes ($CO_2$ evolution noted). The resulting slurry was stirred at 0°–5° C. for an additional 15 minutes, after which time it was filtered under suction. The collected solid was washed with fresh dichloromethane (2×20 ml) and was dried in vacuo at ambient temperature for 23 hours to give 8.58 g (>100%) of crude product.

This material was slurried in 40 ml of deionized water, and the pH was lowered to 0.50 by the addition of 4 N HCl solution. Decolorizing carbon (0.86 g, 10% by weight of crude material) was added, and the resulting slurry was stirred at ambient temperature for 15 minutes. The charcoal was removed by filtration through diatomaceous earth (2.0 g), and the pad was washed with water (1×5 ml). The filtrate was cooled to 0°–5° C., and the pH of the aqueous was raised to 4.0 by dropwise addition of 6 N NaOH solution. After stirring the resulting slurry at 0°–5° C. for 90 minutes, the solid was filtered, washed with cold (0°–5° C.) water (1×10 ml) and was dried in vacuo at ambient temperature for 66 hours. A total of 3.81 g (63%) of (6R,7R)-7-amino-3-[(1H-1-methyltetrazol-5-yl)thio]methylceph-3-em-4-carboxylic acid was isolated as an off-white solid. The 360 MHz $^1$H NMR and IR spectra, and the HPLC chromatogram (86.0% activity versus the standard lot) were consistent with an authentic sample of this material prepared independently.

EXAMPLE 8

(6R,7R)-7-Amino-3-[5-methyl-1,3,4-thiadiazol-2-yl)thio]methylceph-3-em-4-carboxylic Acid

Method A

To a slurry of 1.22 g (9.2 mmoles, 1.0 equivalent) of 2-mercapto-5-methyl-1,3,4-thiadiazole and 0.74 ml (9.2 mmoles, 1.0 equivalent) of dry pyridine (dried over KOH) in 20 ml of dry dichloromethane (dried over molecular sieves) at 0°–5° C. under a blanket of dry nitrogen was added a solution of (6R,7R)-trimethylsilyl 7-(trimethylsilyl)amino-3-iodomethylceph-3-em-4-carboxylate (prepared according to Method A of Example 3; 2.50 g input 7-ACA) in Freon TF over a period of 10 minutes with good stirring. The resulting mixture was stirred at 0°–5° C. for 90 minutes following the addition. Next, 1.5 ml (37.0 mmoles, 4.0 equivalents) of methanol was added dropwise and the resulting slurry was stirred for an additional 10 minutes at 0°–5° C. The solid was collected by suction filtration, washed with fresh Freon TF (2×10 ml) and was dried to constant weight in vacuo to give 4.0 g (>100%) of crude product.

This material was suspended in 10 ml of water and was cooled to 0°–5° C. The pH was lowered to 0.30 by dropwise addition of concentrated HCl solution. To the resulting cloudy solution was added 0.40 g (10% by weight of crude) of decolorizing carbon, and stirring was continued at 0°–5° C. for 15 minutes. The charcoal was removed by filtration and the pH of the clear, yellow filtrate was raised to 3.0 at 0°–5° C. by dropwise addition of solution. The resulting slurry was stirred at 0°–5° C. for 30 minutes. Suction filtration of the solid followed by washing with cold (0°–5° C.) water (2×5 ml) and drying to constant weight in vacuo gave 1.6 g (50%) of (6R,7R)-7-amino-3-[(5-methyl-1,3,4-thiadiazol-2-yl)thio]methylceph-3-em-4-carboxylic acid. The 360 MHz $^1$H NMR spectrum and HPLC chromatogram of this material were consistent with those of an authentic sample prepared independently.

Method B

To a stirred solution of (6R,7R)-trimethylsilyl 7-[((trimethylsilyl)oxy)carbonyl]amino-3-iodomethyl-ceph-3-em-4-carboxylate in dichloromethane (prepared according to Example 4; 5.0 g input 7-ACA) at 0°–5° C. under a blanket of dry nitrogen was added a suspension consisting of 2.43 g (18.4 mmoles, 1.0 equivalent) of 2-mercapto-5-methyl-1,3,4-thiadiazole and 1.49 ml (18.4 mmoles, 1.0 equivalent) of dry pyridine (dried over KOH) in 20 ml of dry dichloromethane (dried over molecular sieves) over a period of 5 minutes. After stirring an additional 3.5 hours at 0°–5° C., a total of 2.5 ml (61.5 mmoles, 3.35 equivalents) of methanol was added ($CO_2$ evolution noted), and stirring was continued at 0°–5° C. for an additional 15 minutes. The solid was collected by suction filtration, was washed with fresh dichloromethane (2×20 ml) and was dried in vacuo at ambient temperature for 19 hours to yield 9.30 g (>100%) of crude product.

Processing of this crude material as described previously for the crude material of Method B of Example 7 afforded 3.81 g (60%) of (6R,7R)-7-amino-3-[(5-methyl-1,3,4-thiadiazol-2-yl)thio]methylceph-3-em-4-carboxylic acid. The 360 MHz $^1$H NMR and IR spectra, and the HPLC chromatogram (80.8% activity versus the standard lot) were consistent with an authentic sample of this material prepared independently.

EXAMPLE 9

(6R,7R)-7-Amino-3-[(1H-1,2,3-triazol-4-yl)thio]methyl-ceph-3-em-4-carboxylic Acid

Method A

This material was prepared exactly as described in Method A of Example 8 except that (a) 1.13 g (9.2 mmoles, 1.0 equivalent) of 1H-4-mercapto-1,2,3-triazole monosodium salt was used in place of the 2-mercapto-5-methyl-1,3,4-thiadiazole, and (b) the slurry of the triazole and pyridine in dichloromethane was added to the solution of (6R,7R)-trimethylsilyl 7-(trimethylsilyl)amino-3-iodomethylceph-3-em-4-carboxylate in Freon TF. The crude product obtained (3.5 g, >100%) was purified as previously described in Method A of Example 7, to yield 1.4 g (49%) of (6R,7R)-7-amino-3-[(1H-1,2,3-triazol-4-yl)thio]methylceph-3-em-4-carboxylic acid. The 360 MHz $^1$H NMR spectrum and HPLC chromatogram were consistent with an authentic sample of this material prepared independently.

Method B

This material was prepared exactly as described in Method B of Example 7 except that 2.26 g (18.4 mmoles, 1.0 equivalent) of 1H-4-mercapto-1,2,3-triazole monosodium salt was used in place of the 1H-5-mercapto-1-methyltetrazole. The crude product obtained (8.40 g, >100%) was purified as previously described in Method B of Example 7, to give 3.25 g (56%) of (6R,7R)-7-amino-3-[(1H-1,2,3-triazol-4-yl)thio]methyl-ceph-3-em-4-carboxylic acid. The 360 MHz $^1$H NMR and IR spectra, and the HPLC chromatogram (79.0% activity versus the standard lot) were consistent with an authentic sample of this material prepared independently.

EXAMPLE 10

(6R,7R)-7-Amino-3-[(1H-1-carboxymethyltetrazol-5-yl)thio]-methylceph-3-em-4-carboxylic Acid

Method A

This material was prepared exactly as described previously in Method A of Example 8 except that 1.47 g (9.2 mmoles, 1.0 equivalent) of 1H-1-carboxymethyl-5-mercaptotetrazole was used in place of the 2-mercapto-5-methyl-1,3,4-thiadiazole. A sample (3.25 g) of the crude product obtained (4.6 g, >100%) was purified as previously described in Method A of Example 8 to give 0.90 g (37%) of (6R,7R)-7-amino-3-[(1H-1 -carboxymethyltetrazol-5-yl)thio]methylceph-3-em-4-carboxylic acid. The 360 MHz H NMR spectrum and HPLC chromatogram were consistent with an authentic sample of this material prepared independently.

Method B

This material was prepared exactly as described in Method B of Example 7 except that (a) 2.94 g (18.4 mmoles, 1.0 equivalent) of 1H-1-carboxymethyl-5-mercaptotetrazole was used in place of the 1H-1-methyl-5-mercaptotetrazole, and (b) the reaction mixture was stirred for 4.5 hours at 0°–5° C. before quenching with 2.5 ml (61.5 mmoles, 3.35 equivalents) of methanol. The crude product obtained (11.03 g, >100%) was purified as previously described in Method B of Example 7 to afford 3.69 g (54%) of (6R,7R)-7-amino-3-[(1H-1-carboxymethyltetrazol-5-yl)thio]methylceph-3-em-4-carboxylic acid. The 360 MHz $^1$H NMR and IR spectra, and the HPLC chromatogram (79.6 area % purity; reference standard not available) were consistent with an authentic sample of this material prepared independently.

EXAMPLE 11

(6R,7R)-7-Amino-3-(pyridinio)methylceph-3-em-4-carboxylic Acid Dihydrochloride

Method A

To a stirred solution of (6R,7R)-trimethylsilyl 7-(trimethylsilyl)amino-3-iodomethylceph-3-em-4-carboxylate in Freon TF (prepared according to Method A of Example 3; 2.50 g input 7-ACA) at 0°–5° C. under a blanket of dry nitrogen was added a solution of 1.6 ml (20.0 mmoles, 2.2 equivalents) of dry pyridine (dried over KOH) in 5 ml of dry Freon TF (dried over molecular sieves) dropwise over a period of 10 minutes. The reaction mixture was stirred for an additional 15 minutes following the addition. After this time, 1.5 ml (37.0 mmoles, 4.0 equivalents) of methanol was added dropwise, and the slurry was stirred at 0°–5° C. for 15 minutes. The solid was collected by suction filtration, washed with fresh Freon TF and dried to constant weight in vacuo to give 3.0 g of crude product. The presence of the desired (6R,7R)-7-amino-3-(pyridinio)-methylceph-3-em-4-carboxylate (as the hydroiodide salt) in this crude material was verified by comparison of the 360 MHz $^1$H NMR spectrum and HPLC chromatogram (34 area % purity) with those of an authentic sample of this material prepared independently; see also Smith, G. C. D., EP 70706, Jan. 26, 1983; pg. 21.

Method B

To a stirred solution of (6R,7R)-trimethylsilyl 7-[((trimethylsilyl)oxy)carbonyl]amino-3-iodomethylceph-3-em-4-carboxylate in dichloromethane (prepared according to Example 4; 5.0 g input 7-ACA) at 0°–5° C. under a blanket of dry nitrogen was added a solution of 3.0 ml (37.0 mmoles, 2.0 equivalents) of dry pyridine (dried over KOH) in 20 ml of dry dichloromethane (dried over molecular sieves) dropwise over 5 minutes. The resulting solution was stirred at 0°–5° C. for an additional 90 minutes, after which time 2.5 ml (61.5 mmoles, 3.35 equivalents) of methanol was added dropwise over 5 minutes such that the temperature remained <10° C. ($CO_2$ evolution noted). The mixture was stirred at 0°–5° C. for an additional 15 minutes. The solid was filtered under suction, washed with fresh dichloromethane (2×20 ml) and was partially dried under suction for 15 minutes. The solid was further dried at ambient temperature in vacuo for 17 hours to give 7.41 g (96%, as the iodide salt) of crude product.

This material was slurried in 25 ml of deionized water and the pH was lowered to 0.50 by dropwise addition of concentrated HCl solution. A total of 0.72 g of decolorizing carbon was added, and the resulting slurry was stirred at ambient temperature for 25 minutes. After this time, the charcoal was removed by filtration through diatomaceous earth (1.0 g), and the pad was washed with water (1×5 ml). To the resulting clear filtrate was added 120 ml (4 volumes) of isopropyl alcohol dropwise with concomitant cooling to 0°–5° C. An additional 180 ml of isopropyl alcohol (total=10 volumes) was added dropwise, and the resulting slurry was stirred at 0°–5° C. for 1 hour. The solid was collected by suction filtration, washed with isopropyl alcohol (2×20 ml) and acetone (1×20 ml) and was partially dried under suction for 15 minutes. Further drying at ambient temperature in vacuo for 16 hours gave a 3.00 g (45%) of (6R,7R)-7-amino-3-(pyridinio)methylceph-3-em-4-carboxylate dihydrochloride. The 360 MHz $^1$H NMR spectrum and HPLC chromatogram (88 area % purity) were consistent with an authentic sample of this material prepared independently; see also Smith, G. C. D., EP 70706, Jan. 26, 1983; pg. 21.

EXAMPLE 12

Attempted Preparation of (6R,7R)-7-Amino-3-(1-Methyl-1-pyrrolidinio)methylceph-3-em-4-carboxylate Monohydrochloride by Sequential Reaction of (6R,7R)-Trimethylsilyl 7-(Trimethylsilyl)amino-3-acetoxymethylceph-3-em-4-carboxylate in Freon TF with Bromotrimethylsilane, N-Methylpyrrolidine and Aqueous HCl Solution To a stirred, slightly cloudy reaction mixture of (6R,7R)-trimethylsilyl 7-(trimethylsilyl)amino-3-acetoxymethylceph-3-em-4-carboxylate (prepared according to Method A of Example 1; 10.0 g input 7-ACA) in Freon TF at ambient temperature under a blanket of dry nitrogen was added 4.5 ml (42.2 mmoles, 1.15 equivalents) of 98% bromotrimethylsilane (Aldrich) in a slow stream over 1 minute. The progress of the reaction was monitored by $^1$H NMR spectroscopy. After stirring 90 minutes at ambient temperature, only a trace of the reaction products (3-bromomethyl cephalosporin and trimethylsilyl acetate) were detected. The reaction was gently heated at reflux under a blanket of nitrogen with reaction progress again being monitored by $^1$H NMR spectroscopy. After 10 days, the predominant species in the reaction mixture were the starting materials. At best, only 15% (by intregration area) conversion to the desired (6R,7R)-trimethylsilyl 7-(trimethylsilyl)amino-3-bromomethylceph-3-em-4-carboxylate te was observed by analysis of the reaction mixture by 360 MHz $^1$H NMR spectroscopy.

EXAMPLE 13

Attempted Preparation of (6R,7R)-7-Amino-3-(1-methyl-1-pyrrolidinio)methyl-ceph-3-em-4-carboxylate Monohydrochloride by Sequential Reaction of (6R,7R)-Trimethylsilyl 7-(Trimethylsilyl)amino-3-acetoxymethylceph-3-em-4-carboxylate in Freon TF with Chlorotrimethylsilane, N-Methylpyrrolidine and Aqueous HCl Solution The procedure for this example was as described in Example 12, except that 5.4 ml (42.2 mmoles, 1.15 equivalents) of chlorotrimethylsilane was used in place of the bromotrimethylsilane. After heating the reaction at reflux for 10 days under a blanket of nitrogen, analysis of the mixture by 360 MHz $^1$H NMR spectroscopy showed mainly chlorotrimethylsilane and (6R,7R)-trimethylsilyl 7-(trimethylsilyl)amino-3-acetoxymethyl-ceph-3-em-4-carboxylate. At best, only 5% (by integration area) conversion to the desired (6R,7R)-trimethylsilyl 7-(trimethylsilyl)amino-3-chloromethylceph-3-em-4-carboxylate was observed.

EXAMPLE 14

(6R,7R)-7-Amino-3-(1-methyl-1-pyrrolidinio)methyl-ceph-3-em-4-carboxylate Hydrochloride or Hydroiodide Via a "One Pot" Reaction Scheme The following is a compendium of experiences and observations derived from several repeated reactions using the same amounts of reactants, temperatures, etc.

Procedure 1. 7-ACA (50.0 g, 0.184 mole) was added into CCl$_2$FCClF$_2$ (Freon TF) (350 ml) under a nitrogen atmosphere (Note 1).

2. HMDS (46.5 ml, 0.22 mole, 1.2 equivalents) was added to this stirred suspension in one portion.

3. TMSI (0.78 ml, 6.0 mmoles, 0.03 equivalent) was added in one portion by means of a syringe (Note 2).

4. The resulting mixture was heated and refluxed for 7–10 hours (Notes 3, 4). The reaction was monitored by NMR (Note 5). CPD personnel will be responsible for determining when the reaction is complete. The appearance of the reaction mixture was a very thin, light yellow slurry.

5. The silylation mixture was cooled to ambient temperature, further diluted with Freon TF (150 ml) and was cooled to 5° C. under a nitrogen blanket.

6. With good stirring, N-methylpyrrolidine, NMP, (26.83 ml, 0.26 mole, 1.4 equivalents) was added over 10 minutes while maintaining a reaction temperature below 10° C. (Note 6).

7. TMSI (47.1 ml, 0.33 mole, 1.8 equivalents) was added at a slow rate over a period of 10–15 minutes by syringe into the well-stirred mixture from Step 6 at 5° C. A small exothermic temperature rise was observed during the TMSI addition. The reaction slurry was stirred at 5° C. for 30 minutes under a blanket of dry nitrogen.

8. The resulting slurry was carefully heated and stirred at 35° C. to 36° C. for a 45–55 hour period. The course of the displacement reaction was monitored by HPLC (Note 7).

9. Both the volume of the reaction mixture and the rate of agitation were checked regularly. An additional 100 ml of Freon TF was added as necessary (Note 8).

10. Upon completion of the reaction (7-ACA less than 2 area % by HPLC), the slurry was cooled to 5° C. under nitrogen protection and methanol (25 ml, 0.615 mole) was added dropwise over an 8 minute period at 5° C. (Note 9).

11. The slurry thinned considerably and was stirred for an additional 15 minutes at 5°–10° C. after methanol was added.

12. The cooling bath was then removed, and 125 ml of 3 N HCl (prepared by adding 250 ml of concentrated HCl solution to 756 ml of water) was added over 2 minutes with good stirring. The reaction temperature rose to 12°–15° C.

13. The hydrolysis mix was warmed to 20°–25° C. as fast as possible (without exceeding 25° C.) and was further stirred at 20°–25° C. for 15 minutes.

14. The phases were separated, and the organic phase (bottom phase) was back extracted with water (1×50 ml). This aqueous phase was used as the wash during the polish filtration of the rich aqueous solution.

15. Diatomaceous earth (2.5 g) was added to the rich aqueous phase from Step 14 and it was filtered through a precoated diatomaceous earth filter (7.5 g). The diatomaceous earth cake was washed with the aqueous solution from Step 14 (back extraction) and then with 25 ml of deionized H$_2$O.

16. The combined rich aqueous solution and wash (volume ca. 270 ml, reddish brown in color) was stirred for 30 minutes at 21°–23° C. with decolorizing carbon (10 g). Diatomaceous earth (2.5 g) was added to the mixture and stirring was continued for 5 minutes.

17. The carbon was removed by filtration through a precoated diatomaceous earth filter (7.5 g). The carbon cake was washed with water (1×75 ml), and was further dried under suction for 5 minutes.

18. If necessary, additional amounts of Freon TF found at the bottom of the rich aqueous solution were separated from the aqueous phase.

19. To the clear, orange colored aqueous solution (volume ca. 350 ml; pH 0.9–1.15) was added isopropyl alcohol (Note 10) dropwise to the cloud point.

20. The isopropyl alcohol addition was stopped, and the crystallization was allowed to proceed at 21°–23° C. for 15 minutes.

21. After this time, additional isopropyl alcohol was added into the slurry over a period of 45 to 60 minutes (a total of 1.2 liters of isopropyl alcohol was added), and then the slurry was stirred and cooled at 0°–5° C. for 60 minutes.

22. The product was collected by filtration, and the cake was washed with cold (0°-b 5° C.) 9/1 isopropyl alcohol/water (2×100 ml, Note 11) and acetone (1×100 ml). The product (Note 12) was dried under suction for an additional 15 minutes. The product was then dried in vacuo to constant weight to give 46–51 g (75–83%) of the crude HCl or HI salt of the title product (Compound I), as a slightly off-white to white crystalline solid. The activity yield was 60–63.4%.

23. The product purities were >95% based on NMR analysis. The HPLC potencies were 750–800 mcg/mg versus an analytical sample of the $\Delta^3$ form of Compound I.HCl. The area % purities were >95%.

Note 1. 7-ACA is an extremely dusty solid. It should be weighed out in a hood or other area with adequate ventilation. A dust respirator and disposable outer garment should be worn as protection from the 7-ACA dust.

Note 2. All operations with TMSI should be performed under anhydrous conditions as much as possible.

Note 3. The reaction time has proven to be variable and is probably dependent on the presence of TMSI (or its reactive equivalent) catalyst. If the reaction appears to be sluggish, additional TMSI hastens the completion of the reaction.

Note 4. It is important that vigorous reflux is maintained, as a major driving force for reaction is the removal of the ammonia that is produced.

Note 5. It is important that anhydrous conditions are maintained when samples are removed from the reaction mixture. This holds true for all reactions in this sequence.

Note 6. A rise in temperature to over 10° C. during the addition of NMP resulted in an enhanced amount of the undesired $\Delta^2$ isomer of 1/26.

Note 7. Samples should be submitted every 4–6 hours for HPLC evaluation. The reaction temperature, time and concentration and the number of equivalents of TMSI and the medium basicity are critical in this reaction.

Note 8. Slurry will become very thick and some dilution of $CCl_2FCClF_2$ will be required to facilitate agitation.

Note 9. Prior to the addition of $CH_3OH$, the slurry is so thick that chunks of material cling to the side of the reaction vessel, making complete mixing with $CH_3OH$ difficult. It should be determined by visual observation that good and completed mixing is occurring throughout the reaction vessel.

Note 10. This usually required 0.5–1.0 volume of isopropanol.

Note 11. This wash was prepared by mixing 90 ml of isopropanol and 10 ml of water and cooling to 0°–5° C. in an ice water bath.

Note 12. In a separate experiment, the product was isolated as the pure HI salt by treating the slurry from Step 11 with 125 ml of 3 N HI instead of 125 ml of 3 N HCl (as in Step 12). Processing of the aqueous phase as described (cf. Steps 13–24) yielded 44.3 g of white, crystalline HI salt. The corrected HPLC potency was 105% versus an analytical standard HCl salt. The activity yield from 7-ACA was 56.7%.

EXAMPLE 15

Recrystallization of (6R,7R)-7-Amino-3-(1-methyl-1-pyrrolidinio)-methyl-ceph-3-em-4-carboxylate Monohydrochloride (Compound I.HCl)

Procedure

1. Crude I.HCl (15.0 g, 0.045 moles) was added in one portion to 1N HCl (125 ml, 3.5 moles, 3.50 equivalents) with good stirring.
2. The resulting mixture was stirred at ambient temperature for 5 minutes.
3. A total of 8.0 g of decolorizing carbon was added in one portion with continued good stirring. The slurry was agitated for an additional 45 minutes.
4. The carbon slurry was filtered under suction through a pad of diatomaceous earth (8.0 g). The pad was washed with water (1×35 ml), and was dried under suction for 5 minutes.
5. The slightly cloudy filtrate was polish filtered through a 5 μm Millipore filter to give a sparkling clear, water-white aqueous filtrate (volume=170 ml).
6. Isopropyl alcohol (125 ml) was added dropwise to the cloud point over a period of 25 minutes with good stirring. At this point, the addition of isopropanol was stopped. The slurry was stirred at ambient temperature for 15 minutes, during which time a good seed bed was established.
7. Additional isopropyl alcohol (475 ml, Note 3) was added dropwise over a period of 25 minutes with good stirring.
8. The resulting slurry was stirred with ice water bath cooling for 1 hour.
9. The slurry was filtered, and was sequentially washed with cold (0°–5° C.) 9/1 isopropanol/water (2×120 ml, Note 4) and acetone (1×120 ml).
10. The filter cake was partially dried under suction for 15 minutes. Further drying in vacuo (steam injector suction) for 15 hours at 40° C. gave 7.87 g (52%) of snow-white, electrostatic, crystalline I.HCl (Note 5).

Note 1. The number of moles of input I.HCl is based on 100% purity.

Note 2. The 1N hydrochloric acid solution was prepared by adding 83 ml of concentrated hydrochloric acid to 920 ml of distilled water.

Note 3. The total volume of isopropyl alcohol used for the crystallization was 600 ml, which was 3.5 times the volume of the polished aqueous filtrate from Step 5.

Note 4. The isopropanol/water washes consisting of 108 ml isopropanol and 12 ml distilled water were cooled to 0°–5° C. in an ice bath.

Note 5. The analytical data complied on the recrystalized I.HCl are shown below:

| ANALYSIS | THEORY | FOUND | CORRECTED FOR KF |
|---|---|---|---|
| % C | 46.77 | 46.02 | 46.71 |
| % H | 6.04 | 6.17 | 6.10 |
| % N | 12.59 | 12.31 | 12.49 |
| % S | 9.61 | 9.50 | 9.64 |
| KF($H_2O$) | — | 1.47 | |
| Residue (sulfated ash) | — | <0.1 | |

This material was assayed at 99.5% potency versus the HPLC standard lot of I.HCl. The Klett number was 3 (100.0 mg sample diluted to 10 ml in a volumetric flask with Milli-Q water; filtered through a Milex HPLC sample preparation filter; blue light; path length ca. 1.2 cm).

In general, it has been found that the "crude" compound I.HCl formed by the addition of HCl to the final mixture, contains some I.HI (formed from the iodide present in the precursor intermediate II). Thus, although it is of high antibacterial purity, it normally must be recrystallized as above to remove Compound I.HI.

On the other hand, the initially crystallized Compound I.HI formed by the addition of HI to the final reaction mixture, is free of Compound I.HCl. Accordingly, the I.HI is normally of high purity and need not be recrystallized.

EXAMPLE 16

Conversion of I, (X=HCl) to (VIII)

A sample of Compound I (X=HCl), (21.72 g, 0.0612 mole), was dissolved in water (190 ml) at 25° C. with stirring. The mixture was then cooled to 8°–10° C., and the pH adjusted from 2.5 to 5.8 (range 5.7–5.9) by the dropwise addition of sodium hydroxide solution (2 N, 30.5 ml, 0.061 mole, 1.0 equivalent). Total volume was 214 ml.

Tetrahydrofuran (THF, 555 ml) was then added in three portions. The temperature of the mixture after each addition rose to 12°-13° C. and was allowed to return to 8°-10° C. before the next portion was added. The total addition time was 10 minutes. The pH of the mixture was 5.8-6.1.

The pH of the mixture was then adjusted to 6.8 (range 6.7-6.9) by the dropwise addition of sodium hydroxide solution (2 N, 2.0 ml, 0.004 mole).

A sample of the 1-benzotriazol (Z)-2-(2-aminothiazol-4-yl)-2-methoxyiminoacetate active ester (29.5 g, 0.0927 mole) was added to the reaction mixture in five equal portions over 45 minutes. The cooling bath was removed after the first portion of the active ester had been added. The pH of the reaction mixture was readjusted to 6.5 (range 6.5-6.7) 5-10 minutes after each addition of the active ester by the dropwise addition of sodium hydroxide solution (2 N).

The clear, pale orange reaction mixture was stirred for 2-3 hours at 25° C. In the initial 30 minutes, the pH was readjusted to 6.5 (range 6.5-6.7) every 5-10 minutes by the dropwise addition of 2 N sodium hydroxide solution. In the remaining reaction time, the pH was readjusted to 6.5 every 15 minutes (total 2 N NaOH: 29.5 ml, 0.059 mole, 0.97 equivalent). The completion of the reaction was judged by HPLC analysis.

Solids present in the reaction mixture were then removed by filtration and washed with water (2×5 ml). The filtrate was extracted with methyl isobutyl ketone (MIBK, 790 ml) and the aqueous layer separated. The organic phase was washed with water (64 ml), and the aqueous phases combined and stirred with Dicalite (5.1 g) for 10 minutes. The solids were removed by suction filtration and washed with water (2×5 ml).

The resulting clear orange solution (volume 314 ml) was acidified with good stirring to pH 3.7 (range 3.5-4.0) by the dropwise addition of sulfuric acid (4N, 14.5 ml). At this point the mixture became cloudy and crystallization of the sulfuric acid addition salt of (VIII) began.

The crystallization was allowed to proceed for 10-15 minutes, and then the pH was adjusted to 3.0 (range 2.9-3.1) by the dropwise addition of sulfuric acid (4N, 7.5 ml). The mixture was cooled to 0 to 5° C. and the remaining sulfuric acid (4N, 63.5 ml) was added over 20-30 minutes (resulting pH: 1.3-1.5). After the addition of sulfuric acid was complete, the slurry was stirred for 1 hour at 0 to 5° C.

The white crystalline product was removed by suction filtration and washed with sulfuric acid (0.5N, 63.5 ml). The solids were partially dried under suction for 15 minutes and then washed with acetone (2×100 ml). The solids were again partially dried under suction for 10 minutes and then slurried for 1 hour in acetone (400 ml) with good agitation. The solids were removed by suction filtration, washed with acetone (2×100 ml) and dried in vacuo (10-15mm Hg) at 35°-40° C. to constant weight (3-6 hours).

The product, the sulfuric acid addition salt of (VIII), was recovered as a slightly electrostatic, white crystalline solid (28.79 g, 81.4%).

EXAMPLE 17

Conversion of I (X =HI) to (VIII)

The general procedure of Example 16 is repeated except that the I (X =HCl) starting material is replaced by an equimolar amount of I (X =HI), and the title compound is thereby produced.

Further Detailed Description of the Invention

EXAMPLE 18

(6R,7R)-Trimethylsilyl 7-(Trimethylsilyl)amino-3-acetoxy methylceph-3-em-4-carboxylate

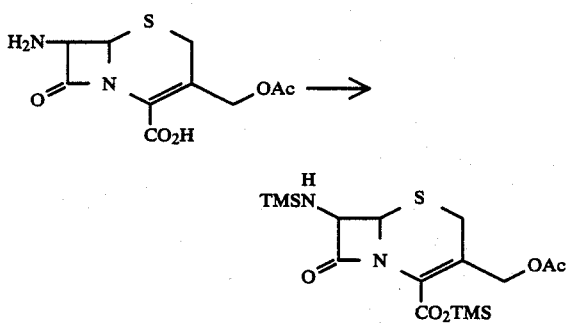

An oven-dried flask and Friedrich's condenser were cooled to ambient temperature under a stream of dry nitrogen. The flask was then charged with 10.0 g(36.7 mmoles) of 7-ACA (97.2% purity) and 70 ml of dry 1,1,2-trichloro-trifluorethane (Freon TF, dried over molecular sieves). To the resulting slurry was added 9.3 ml (44.1 mmoles, 1.2 equivalents) of 98% 1,1,1,3,3,3-hexamethyl-disilazane (HMDS) and 0.16 ml (1.1 mmoles, 0.03 equivalents) of iodotrimethylsilane (TMSI) by syringe with good stirring and with protection from moisture. The slurry was vigorously heated under reflux for 7-10 hours with a slight nitrogen sweep through the system. The reaction was then cooled to ambient temperature under a blanket of dry nitrogen, and was diluted with 30 ml of fresh Freon TF. A $^1$H NMR spectrum of an aliquot of the slightly hazy reaction mixture showed >95% conversion to the desired product which is identical to the product of Example 1, and the $^1$H NMR data is the same as reported in Example 1 Method A.

EXAMPLE 19

(6R,7R)-7-Amino-3-(1-methyl-1-pyrrolidinio)methyl-ceph-3-em-4-carboxylate monohydroiodide

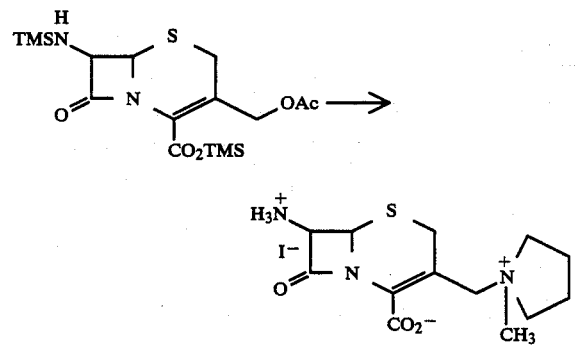

To a slightly hazy solution of (6R,7R)-trimethylsilyl 7-(trimethylsilyl) -amino-3-acetoxymethylceph-3-em-4-carboxylate in Freon TF (prepared according to Example 18) at 0°-5° C. under a blanket of dry nitrogen was added 5.35 ml (51.4 mmoles, 1.4 equivalents) of dry 97% N-methylpyrrolidine (dried over molecular sieves) dropwise over 1-2 minutes with good stirring. Next, 9.40 ml (66.1 mmoles, 1.8 equivalents) of TMSI was added by syringe over about 5 minutes with continued good stirring. The reaction temperature was kept below 10° C. during the addition. The resulting slurry was stirred at 0°-5° C. for an additional 30 minutes. After this time, the slurry was placed into an oil bath carefully maintained at 35°-36° C. The progress of the reaction was monitored by HPLC. After 45-48 hours, the reaction was complete (<2 area % 7-ACA) and it was cooled to 0°14 5° C. under a blanket of dry nitrogen. A total of 5.0 ml (123 mmoles, 3.35 equivalents) of methanol was added dropwise with good stirring. The reaction temperature was maintained at <10° C. during the addition. The resulting slurry was stirred at 0°-5° C. for an additional 15 minutes. Next, 25 ml (75 mmoles, 2.0 equivalents) of 3N aqueous HI solution was added in one portion. Following the addition, the cooling bath was removed, and the 2 phase mixture was rapidly warmed to 20°-25° C. Vigorous stirring was continued for 15 minutes. The phases were separated, and the organic phase was back extracted with water (1×10 ml). This back wash was saved for later use.

The main aqueous phase was stirred at 20°-25° C. for 10 minutes with 0.5 g of diatomaceous earth. The slurry was filtered through 1.5 g of diatomaceous earth (pre-washed with 50 ml water). The pad was washed with the aqueous back wash from above, then with water (1×5 ml). The cake was partially dried under suction for 5 minutes. A total of 2.0 g of decolorizing carbon was added and the slurry was stirred at 20°-25° C. for 30 minutes. After this time, 0.5 g of diatomaceous earth was added and stirring was continued for an additional 5 minutes. The slurry was filtered through 1.5 g of diatomaceous earth (pre-washed with 50 ml water), and the pad was washed with water (1×5 ml). The diatomaceous earth pad was partially dried under suction for 5 minutes. The filtrate was polish filtered through a 5 μm Millipore filter.

Precipitation of the product was achieved by drop-wise addition of 3.5 volumes of isopropanol to the clear, amber-colored aqueous phase at 20°-25° C. The resulting slurry was cooled to 0°-5° C. and was allowed to stand for 1 hour. The slurry was filtered and washed with cold (0°-5° C) isopropanol/water (4/1;v/v) (2×20 ml) and acetone (2×20 ml). The cake was partially dried under suction for 5 minutes. Further drying in vacuo at 20°-25° C. to constant weight afforded 8.94 g (57%) of white, crystalline (6R,7R)-7-amino-3-(1-methyl-1-pyrrolidinio) methylceph-3-em-4-carboxylate monohydroiodide. HPLC showed the salt to be 97 area % pure; and the 360 MHz $^1$H NMR spectrum observed for the title compound as a monohydroiodide is the same as the $^1$H NMR data reported for the HCl salt of the identical product in Example 6, Method A.

EXAMPLE 20

(6R,7R)-7-Amino-3-(4-methyl-4-morpholinio)methyl-ceph-3-em-4-carboxylate monohydroiodide

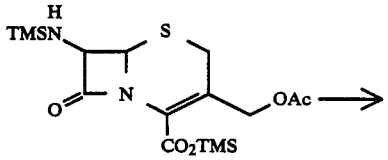

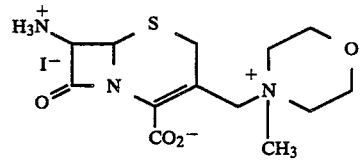

The title compound was prepared from a Freon TF solution of (6R,7R)-trimethylsilyl 7-(trimethylsilyl)amino-3-acetoxymethyceph-3-em-4-carboxylate (from 50.0 g input 7-ACA) as described in Example 19, except that 28.3 ml (257 mmoles, 1.4 equivalents) of dry N-methylmorpholine (dried over molecular sieves) was substituted for the N-methylpyrrolidine. The progress of the reaction was monitored by HPLC and was found to be complete after 7-8 hours at 35°-36° C. The reaction was worked up as described in Example 19 (amounts of materials are multiplied by 5× due to increased batch size) to afford 36.0 g (41%) of slightly off-white crystalline 6R,7R)-7-amino-3-(4-methyl morpholinio)methylceph-3-em-4-carboxylate monohydroiodide. HPLC area % purity was >95%; $^1$H NMR (360 MHz, D$_2$O) δ3.30(s, 3H, N-CH$_3$), 3.60(m, 4H, $$-\overset{+}{\text{N}}(\text{CH}_3)\underline{\text{CH}_2}\text{CH}_2\text{OCH}_2\underline{\text{CH}_2}),$$

3.68(d, 1H, J=10 Hz, —SCH$_2$—), 4.04(d, 1H, J=10 Hz, —SCH$_2$—), 4.2 (m, 4H, $$-\overset{+}{\text{N}}(\text{CH}_3)\text{CH}_2\underline{\text{CH}_2}\text{OC}\underline{\text{H}_2}\text{CH}_2),$$

4.25 (d, 1H, J=14 Hz,

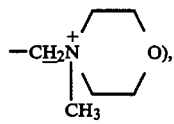

4.93 (d, 1H, J=14 Hz,

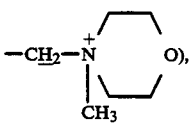

β-5.30 (d, 1H, J=5Hz, C-6 β-lactam), 5.53 (d, 1H, J=5Hz, C-7 β-lactam);

IR (KBr) 3460, 1795 and 1600 cm$^{-1}$.

Anal. Calc'd for C$_{13}$H$_{19}$N$_3$O$_4$S.HI: C, 35.40; H, 4.34; N, 9.53; Found: C, 34.99; H, 4.38; N, 9.35;

EXAMPLE 21

(6R,7R)-7-Amino-3-(1-pyridinio)methylceph-3-em-4-carboxylate monohydroiodide

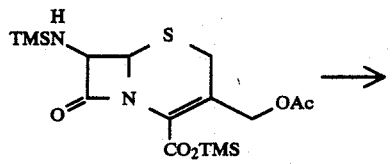

The title compound was prepared from a solution of (6R,7R)-trimethylsilyl 7-(trimethylsilyl)amino-3-acetoxy-methyceph-3-em-4-carboxylate in Freon TF (10.0 g input 7-ACA) as described in Example 19, except that 4.2 ml (51.4 mmoles, 1.4 equivalents) of dry pryidine (dried over KOH) was substituted for the N-methyl-pyrrolidine. The progress of the reaction was monitored by HPLC and was found to be complete after 51 hours at 35°-36° C. The slurry was cooled to 20°-25° C. under a blanket of dry nitrogen. The solid was removed by filtration through a funnel under positive nitrogen pressure. The collected solid was washed with fresh Freon TF (2×100 ml). The filtercake was quickly added to 50 ml of dry dichloromethane which was pre-cooled to 0°-5° C. in an ice-water bath. To the resulting dark solution was added 5.0 ml (123 mmoles, 3.35 equivalents) of methanol dropwise with good stirring and with a reaction temperature of <10° C. The resulting slurry was stirred at 0°-5° C. for an additional 15 minutes. The solid was collected by filtration and was washed with fresh $CH_2Cl_2$ (2×50 ml). The filtercake was reslurried in 150 ml $CH_2Cl_2$ for 1 hour. The solid was filtered, washed with $CH_2Cl_2$ (2×50 ml) and dried in vacuo at 20°-25° C. to constant weight to afford 14.7 g (95%) of crude (6R,7R)-7-amino-3-(1-pyridinio)methylceph-3-em-4-carboxylate monohydroiodide. The 360 MHz $^1H$ NMR spectrum and HPLC chromatogram (65 area % purity; major contaminant was pyridine hydroiodide, 13 area %) of this material were consistent with an authentic sample prepared independently; see also Smith, G.C.D., EP-70706, Jan. 26, 1983; pg. 21).

EXAMPLE 22

(6R,7R)-7-Amino-3-[1-(2,3-cyclopenteno)pyridinio]methylceph-3-em-4-carboxylate monohydroidide

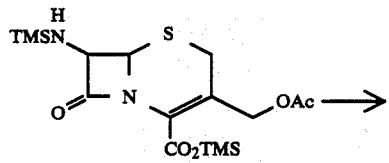

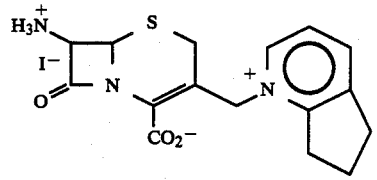

The title compound was prepared from a solution of (6R,7R)-trimethylsilyl 7-(trimethylsilyl)amino-3-acetoxymethylceph -3-em-4-carboxylate in Freon TF (10.0 g input 7-ACA) as described in Example 19, except that 6.02 ml (51.4 mmoles, 1.4 equivalents) of 2,3-cyclopentenopyridine (dried over molecular sieves) was substituted for the N-methylpyrrolidine. The progress of the reaction was monitored by HPLC and was found to be complete after 52 hours at 35°-36° C. Work-up of the reaction mixture as described previously in Example 21 afforded 13.2 g (78%) of crude (6R,7R)-7-amino-3-[1-(2,3-cyclopenteno)pyridinio]methylceph-3-em-4-carboxylate monohydroiodide. The 360 MHz $^1H$ NMR spectrum and HPLC chromatogram (92 area % purity) of this material were consistent with an authentic sample of this material prepared independently.

EXAMPLE 23

(6R,7R)-7-Amino-3-[1-(2-acetoxy)ethyl-1-pyrrolidinio]-methylceph -3-em-4-carboxylate monohydroiodide

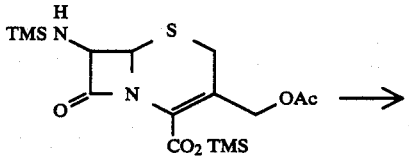

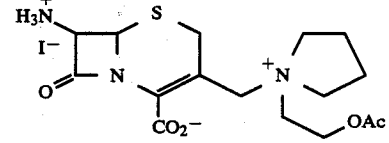

The title compound was prepared from a solution of (6R,7R)-trimethylsilyl 7-(trimethylsilyl)amino-3-acetoxymethylceph -3-em-4-carboxylate in Freon TF (10.0 g input 7-ACA) as described in Example 19, except that 8.08 g (51.4 mmoles, 1.4 equivalents) of N-(2-acetoxy)ethylpyrrolidine was substituted for the N-methylpyrrolidine. The progress of the reaction was monitored by HPLC. During the first 22 hours at 35°-36° C., the reaction mixture oiled out. After a total of 48 hours at 35°-36° C., no further consumption of starting material was evident. The reaction mixture was cooled to 0°-5° C. under a blanket of dry nitrogen. A total of 7.45 ml (184 mmoles, 5.0 equivalent) of methanol was added dropwise as a solution in 50 ml of Freon TF. A reaction temperature of <10° C. was maintained during the addition. The resulting slurry was stirred for 3.5 hours at 0°-5° C. following the addition. The slurry was filtered under suction, and the filtercake was washed with Freon TF (2×50 ml). Further drying in vacuo at 20°-25° C. to constant weight afforded 27.9 g (>100%) of crude product. The presence of the desired (6R,7R)-7-amino-3-[1-(2-acetoxy)ethyl-1-pyrrolidinio]- methylceph-3-em-4-carboxylate monohydroiodide in this crude material was verified by comparison of the 360 MHz ¹H NMR spectrum and HPLC chromatogram of this material with spectra of this material prepared by an independent procedure. The 360 MHz ¹H NMR spectrum showed a $\Delta^3/\Delta^2$ product ratio of 1/1.7 as well as a significant amount of the starting amine. The HPLC chromatogram showed 24 area % of the desired $\Delta^3$-isomer and 34 area % of the $\Delta^2$-isomer were present in the crude solid.

EXAMPLE 24

(6R,7R)-7-Amino-3[1-2(trimethylsilyoxy)ethyl-1-pyrrolidinio]-methylceph-3-em-4-carboxylate monohydroiodide

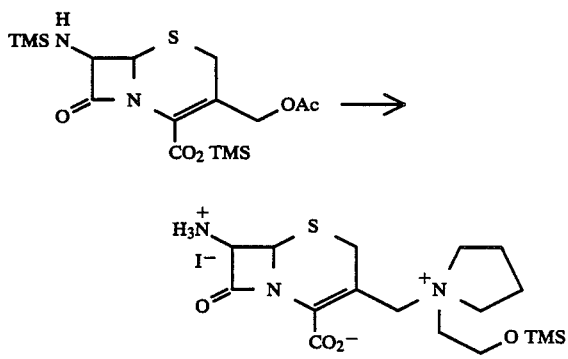

The title compound was prepared from a solution of (6R,7R)-trimethylsilyl 7-(trimethylsilyl)amino-3-acetoxymethylceph-3-em-4-carboxylate in Freon TF (10.0 g input 7-ACA) as described in Example 19, except that 9.63 g (51.4 mmoles, 1.4 equivalents) of N-(2-trimethylsiloxy)ethylpyrrolidine was substituted for the N-methylpyrrolidine. The progress of the reaction was monitored by HPLC. The $\Delta^3/\Delta^2$ mixture of the title compund produced was detected was the free OH compounds due to hydrolysis of the TMS ether during the chromatographic analysis. During the first 23 hours at 35°-36° C., the reaction mixture oiled out. After a total of 30 hours at 35°-36° C., no further consumption of starting material was evident. The reaction was worked up exactly as described in Example 23 to afford 29.77 g (>100%) of crude product. The presence of the desired (6R,7R)-7-amino-3-[1-(2-trimethylsiloxy)ethyl-1-pyrrolidinio]methylceph-3-em-4-carboxylate monohydroiodide in this crude material was verified by comparison of the 360 MHz ¹H NMR spectrum and HPLC chromatogram of this material with spectra of this material prepared by an independent procedure. The 360 MHz ¹H NMR spectrum showed a $\Delta^3/\Delta^2$ product ratio of 1/3.3 as well as a significant amount of the starting amine. The HPLC chromatogram showed 16 area % of the desired $\Delta^3$-isomer and 60 area % of the $\Delta^2$-isomer were present in the crude solid.

EXAMPLE 25

7-[α-(2-Aminothiazol-4-yl)-α-(Z)-methoxyiminoacetamido]-3-[(1-methyl-1-pyrrolidinio)methyl]-3-cephem-4-carboxylate

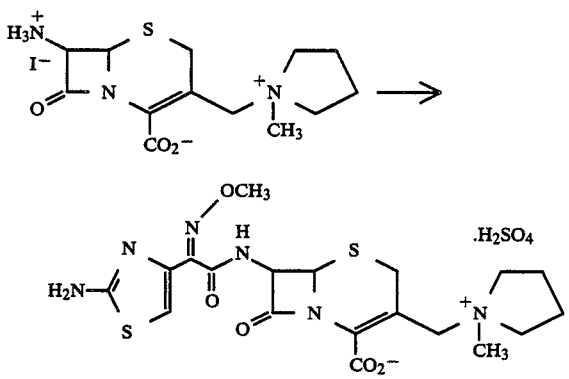

A total of 12.76 g (30 mmoles) of (6R,7R)-7-amino-3-(1-methyl-1-pyrrolidinio)methylceph -3-em-4-carboxylate monohydroiodide (prepared in Example 19) was suspended in 87 ml of water with good stirring at 20°-25° C. The slurry was cooled to 8°-10° C., and the pH was raised to 5.80 at 7° C. by dropwise addition of 13.0 ml (26 mmoles, 0.87 equivalents) of 2N sodium hydroxide solution over a period of 35 minutes. Next, 555 ml of tetrahydrofuran was added, and the pH of the resulting solution was increased to 6.8 at 10° C. by dropwise addition of 1.9 ml (3.8 mmoles, 0.13 equivalents) of 2N sodium hydroxide solution. The cooling bath was removed, and 29.5 g (92.7 mmoles, 1.5 equivalents) of the HOBT active ester of syn-2-(2-aminothiazol-4-yl) -2-methoxyiminoacetic acid was added in two equal portions of 14.75 g each over 30 minutes. Following each addition, the pH was readjusted to 6.5 every 5-10 minutes, by dropwise addition of 2N sodium hydroxide solution. In the remaining reaction time, the pH was readjusted to 6.5 by dropwise addition of 2N sodium hydroxide solution every 15 minutes (total 2N sodium hydroxide used was 28.6 ml (57.2 mmoles, 1.91 equivalents). The completion of the reaction was determined by HPLC analysis.

After 1.75 hours the dark solution was poured into 365 ml of methyl isobutyl ketone, and the lower aqueous phase was separated. The organic phase was back extracted with water (1×30 ml). The combined aqueous phases were stirred 10 minutes at 20°-25° C. with 2.35 g of diatomaceous earth. The insoluble material was removed by suction filtration, and the filtercake was washed with water (1×5 ml). The amber colored aqueous phase was polish filtered through a 5μm Millipore filter. The pH of the solution was 6.40 at 17° C.

A total of 6.7 ml of 4N sulfuric acid was added dropwise with good stirring to give a turbid solution of pH 3.82 at 18° C. Crystallization of the product was allowed to proceed for 5 minutes with good stirring. An additional 3.5 ml of 4N sulfuric acid was added to give a slurry of pH 3.09 at 20° C. The slurry was cooled to 0°-5° C. and a total of 30 ml of 4N sulfuric acid was added dropwise over 20 minutes. The resulting slurry was stirred for 1 hour at 0°-5° C. The precipitate was filtered and washed with 0.5N sulfuric acid (1×30 ml). The filtercake was partially dried under suction for 15 minutes. After this time, the cake was washed with acetone (2×50 ml), and was again partially dried under suction for 15 minutes. The cake was reslurried in 200 ml of acetone at 20°-25° C. or 1 hour. The salt was filtered, washed with acetone (2×50 ml) and was partially dried under suction for 15 minutes. Further drying in vacuo at 40° C. to constant weight gave 12.41 g (72%) of crystalline, slightly off-white title compound as its sulfate salt: $^1$HNMR (360 MHz, D$_2$O with solvent suppression) δ2.16–2.33 (envelope, 4H,

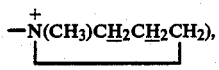

3.01 (s, 3H, N-CH3), 3.45-3.64 (m, 5H,

—SCH$_2$—), 3.95 (d, 1H, J=17 Hz, —SCH$_2$—), 4.04 (d, 1H, J=14 Hz,

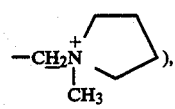

4.08 (s, 3H, —OCH$_3$), 4.75 (d, 1H, J=14 Hz,

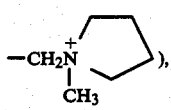

5.37 (d, 1H, J=5 Hz, C-6 β-lactam), 5.86 (d, 1H, J=5 Hz, C-7 β-lactam), 7.16 (s, 1H, C-5 thiazole).

Anal. Calc'd for C$_{19}$H$_{24}$N$_6$O$_5$S$_2$.H$_2$SO$_4$: C, 39.43; H, 4.53; N, 14.53; S, 16.63; Found: C, 39.40; H, 4.47; N, 14.39; S, 16.60

EXAMPLE 26

7-[α-(2-Aminothiazol-4-yl)-α-(Z)-methoxyiminoacetamido]-3-[(4-methyl-4-morpholinio)methyl]-3-cephem-4-carboxylate

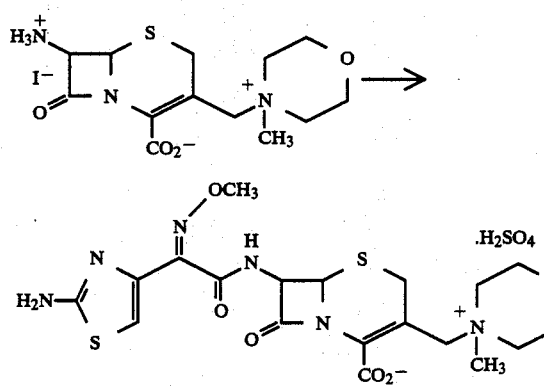

The title compound was prepared from 54.0 g (122 mmoles) of (6R,7R)-7-amino-3-(4-methyl-4-morpholinio)methylceph-3-em-4-carboxylate monohydroiodide (prepared in Example 20) and 59.0 g (184 mmoles, 1.5 equivalents) of syn-2-(2-aminothaizole-4-yl)-2-methoxyiminoacetic acid HOBT active ester by the procedure described in Example 25. A total of 60.1 g (84%) of crystalline, white title compound as its sulfate salt was prepared by this procedure: $^1$H NMR (360 MHz, D$_2$O/NaDCO$_3$) δ3.30 (s, 3H, NCH$_3$), 3.55 (m, 5H,

4.05 (d, 1H, J=16 Hz, —SCH2—), 4.10 (s, 3H, -OCH3, 4.1 (m, 4H,

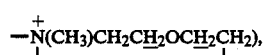

4.21 (d, 1 H, J=14 Hz,

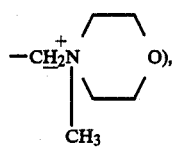

4.95 (d, 1 H, J=14 Hz,

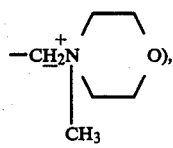

5.47 (d, 1 H, J=5 Hz, C-6 β-lactam), 5.96 (d, 1 H, J=5 HZ, C-7 ⊖-lactam), 7.10 (s, 1 H, C-5 thiazole).

Anal. Calc'd for C$_{19}$ H$_{24}$N$_6$O$_6$S$_2$SO$_4$: C, 38.37; H, 4.41; N, 14.13; S, 16.18; Found: C, 38.16; H, 4.32; N, 14.08; S, 16.14.

EXAMPLE 27

The following Table provides a summary of results for some of the Examples in the present invention. With the exception of compounds of Examples 19 and 20, the reported data are for crude HI salts isolated by filtration of the slurry obtained from the methanol quench. Compounds of Examples 19 and 20 were isolated after quenching the methanol slurry with aqueous 3N HI.

TABLE

| Compound of Example No. | % Yield | Δ$^3$-HPLC Area % Purity | Δ$^3$/Δ$^2$ Ratio HPLC$^a$ | NMR$^b$ |
|---|---|---|---|---|
| 19 | 57 | 97 | 97/0 | — |
| 20 | 41 | >95 | >95/0 | — |
| 21 | 95 | 65$^c$ | 65/6 | — |
| 22 | 78 | 92 | 92/0 | — |
| 23 | >100$^d$ | 24 | 24/34 | 1/1.7 |
| 24 | >100$^d$ | 16 | 16/60 | 1/3.3 |

$^a$Reported data is area % for each isomer in the HPLC chromatograms of the isolated HI salt.
$^b$Reported data is the isomer ratio obtained by comparative integration of a baseline resolved peak(s) for each isomer.
$^c$The major contaminant was the HI salt of pyridine (24 area %).
$^d$The 360 MHz spectrum of the crude HI salt showed the major contaminant to be unreacted starting amine.

Othe variations will be evident to those skilled in the art. Therefore, the scope of the invention is intended to be defined by the claims.

We claim:

1. Stable, crystalline (6R,7R)-7-amino-3-(1-methyl-1-pyrrolidinio) methylceph-3-em-4-carboxylate hydroiodide which is substantially free of the Δ$^2$ isomer.

* * * * *